US012680111B2

(12) United States Patent
Wang et al.

(10) Patent No.: US 12,680,111 B2
(45) Date of Patent: *Jul. 14, 2026

(54) SYNTHETIC PROMOTERS FOR GENE THERAPY AND PROTEIN EXPRESSION

(71) Applicant: University of Massachusetts, Westborough, MA (US)

(72) Inventors: Yang Wang, Wellesley, MA (US); Mark S. Klempner, Boston, MA (US); Monir Ejemel, Medfield, MA (US); Qi Li, Westwood, MA (US); Zuoshang Xu, Wellesley, MA (US)

(73) Assignee: University of Massachusetts, Westborough, MA (US)

( * ) Notice: Subject to any disclaimer, the term of this patent is extended or adjusted under 35 U.S.C. 154(b) by 376 days.

This patent is subject to a terminal disclaimer.

(21) Appl. No.: 18/281,703

(22) PCT Filed: Mar. 11, 2022

(86) PCT No.: PCT/US2022/019976
§ 371 (c)(1),
(2) Date: Sep. 12, 2023

(87) PCT Pub. No.: WO2022/192687
PCT Pub. Date: Sep. 15, 2022

(65) Prior Publication Data
US 2024/0043872 A1 Feb. 8, 2024

Related U.S. Application Data

(60) Provisional application No. 63/160,415, filed on Mar. 12, 2021.

(51) Int. Cl.
*C12N 15/86* (2006.01)
*A61K 48/00* (2006.01)

(52) U.S. Cl.
CPC .......... *C12N 15/86* (2013.01); *A61K 48/0066* (2013.01); *C12N 2750/14143* (2013.01); *C12N 2750/14171* (2013.01); *C12N 2830/15* (2013.01)

(58) Field of Classification Search
None
See application file for complete search history.

(56) References Cited

U.S. PATENT DOCUMENTS

| | | | |
|---|---|---|---|
| 11,674,154 B2 * | 6/2023 | Shim ................... | A61K 48/005 |
| | | | 514/44 R |
| 2004/0047847 A1 | 3/2004 | He et al. | |
| 2009/0280533 A1 * | 11/2009 | Gorfien ................... | C12N 7/00 |
| | | | 435/69.1 |
| 2017/0130244 A1 | 5/2017 | Yang et al. | |
| 2020/0123574 A1 | 4/2020 | Sah et al. | |

FOREIGN PATENT DOCUMENTS

WO WO-2020/236815 A1 11/2020

OTHER PUBLICATIONS

Kaplan, et al. Granting immunity to FOP and catching heterotopic ossification in the Act. Seminars in Cell & Developmental Biology. 2016; 49:30-36. (Year: 2016).*
International Preliminary Report on Patentability for PCT/US2022/019976, dated Sep. 12, 2023 (7 pages).
International Search Report and Written Opinion for PCT/US2022/019976, dated Jun. 16, 2022 (14 pages).

* cited by examiner

*Primary Examiner* — Allison M Fox
*Assistant Examiner* — Gina Pronzati
(74) *Attorney, Agent, or Firm* — Clark & Elbing LLP

(57) ABSTRACT

The invention provides synthetic promoters and methods of using the same.

19 Claims, 6 Drawing Sheets
Specification includes a Sequence Listing.

3 weeks after I.T. Injection 3 weeks after I.T. Injection 4 weeks after I.M. injection scAAV promoter

SEQUENCE LISTING

```
<160> NUMBER OF SEQ ID NOS: 12

<210> SEQ ID NO 1
<211> LENGTH: 379
<212> TYPE: DNA
<213> ORGANISM: Artificial Sequence
<220> FEATURE:
<223> OTHER INFORMATION: Synthetic Construct

<400> SEQUENCE: 1
tcagatcgcc tggagacgcc atccacgctg ttttgacctc catagaagac accgggaccg      60
atccagcctc cgcggccggg aacggtgcat tggaacgcgg attccccgtg ccaagagtga     120
cgtaagtacc gcctatagag tctataggcc cacccccttg gcttcttatg catgctatac     180
tgtttttggc ttggggtcta tacacccccg cttcctcatg tttgctgccc gtgaccagca     240
cgtcaacgat tttgtgggca cgggcgacac cgcagtgtag tctgagcagt actcgttgct     300
gccgcgcgcg ccaccagaca taatagctga cagactaaca gactgttcct ttccatgggt     360
cttttctgca gtcaccgtc                                                  379

<210> SEQ ID NO 2
<211> LENGTH: 962
<212> TYPE: DNA
<213> ORGANISM: Artificial Sequence
<220> FEATURE:
<223> OTHER INFORMATION: Synthetic Construct

<400> SEQUENCE: 2
cgtttagtga accgtcagat cgcctggaga cgccatccac gctgtttga cctccataga      60 agacaccggg accgatccag cctccgcggc cgggaacggt gcattggaac gcggattccc     120
cgtgccaaga gtgacgtaag taccgcctat agagtctata ggcccacccc cttggcttct     180
tatgcatgct atactgtttt tggcttgggg tctatacacc cccgcttcct catgttatag     240
```

-continued gtgatggtat agcttagcct ataggtgtgg gttattgacc attattgacc actcccctat        300
tggtgacgat actttccatt actaatccat aacatggctc tttgccacaa ctctctttat        360
tggctatatg ccaatacact gtccttcaga gactgacacg gactctgtat ttttacagga        420
tggggtctca tttattattt acaaattcac atatacaaca ccaccgtccc cagtgcccgc        480
agtttttatt aaacataacg tgggatctcc acgcgaatct cgggtacgtg ttccggacat        540
gggctcttct ccggtagcgg cggagcttct acatccgagc cctgctccca tgcctccagc        600
gactcatggt cgctcggcag ctccttgctc ctaacagtgg aggccagact taggcacagc        660
acgatgccca ccaccaccag tgtgccgcac aaggccgtgg cggtagggta tgtgtctgaa        720
aatgagctcg gggagcgggc ttgcaccgct gacgcatttg aagacttaa ggcagcggca        780 gaagaagatg caggcagctg agttgttgtg ttctgataag agtcagaggt aactcccgtt        840
gcggtgctgt taacggtgga gggcagtgta gtctgagcag tactcgttgc tgccgcgcgc        900
gccaccagac ataatagctg acagactaac agactgttcc tttccatggg tctttctgc        960 ag                                                                       962

<210> SEQ ID NO 3
<211> LENGTH: 380
<212> TYPE: DNA
<213> ORGANISM: Artificial Sequence
<220> FEATURE:
<223> OTHER INFORMATION: Synthetic Construct

<400> SEQUENCE: 3
gacattgatt attgactagt tattaatagt aatcaattac ggggtcatta gttcatagcc         60
catatatgga gttccgcgtt acataactta cggtaaatgg cccgcctggc tgaccgccca        120 acgaccccg cccattgacg tcaataatga cgtatgttcc catagtaacg ccaatagga         180 ctttccattg acgtcaatgg gtggagtatt tacggtaaac tgcccacttg gcagtacatc        240
aagtgtatca tatgccaagt acgccccta ttgacgtcaa tgacggtaaa tggcccgcct        300
ggcattatgc ccagtacatg accttatggg actttcctac ttggcagtac atctacgtat        360
tagtcatcgc tattaccatg                                                     380

<210> SEQ ID NO 4
<211> LENGTH: 279
<212> TYPE: DNA
<213> ORGANISM: Artificial Sequence
<220> FEATURE:
<223> OTHER INFORMATION: Synthetic Construct

<400> SEQUENCE: 4
tggtcgaggt gagccccacg ttctgcttca ctctccccat ctcccccccc tccccacccc         60
caattttgta tttatttatt ttttaattat tttgtgcagc gatggggcg gggggggggg        120 ggggcgcgc gccaggcggg gcggggcggg gcgaggggcg gggcggggcg aggcggagag        180
gtgcggcggc agccaatcag agcggcgcgc tccgaaagtt tccttttatg gcgaggcggc        240
ggcggcggcg gccctataaa aagcgaagcg cgcggcggg                               279

<210> SEQ ID NO 5
<211> LENGTH: 204
<212> TYPE: DNA
<213> ORGANISM: Artificial Sequence
<220> FEATURE:
<223> OTHER INFORMATION: Synthetic Construct

<400> SEQUENCE: 5

-continued

```
gtgatgcggt tttggcagta catcaatggg cgtggatagc ggtttgactc acggggattt       60
ccaagtctcc accccattga cgtcaatggg agtttgtttt ggcaccaaaa tcaacgggac      120
tttccaaaat gtcgtaacaa ctccgcccca ttgacgcaaa tgggcggtag cgtgtacgg       180 tgggaggtct atataagcag agct                                             204

<210> SEQ ID NO 6
<211> LENGTH: 1011
<212> TYPE: DNA
<213> ORGANISM: Artificial Sequence
<220> FEATURE:
<223> OTHER INFORMATION: Synthetic Construct

<400> SEQUENCE: 6
gacattgatt attgactagt tattaatagt aatcaattac ggggtcatta gttcatagcc       60
catatatgga gttccgcgtt acataactta cggtaaatgg cccgcctggc tgaccgccca      120 acgaccccg cccattgacg tcaataatga cgtatgttcc catagtaacg ccaataggga       180
ctttccattg acgtcaatgg gtggagtatt tacggtaaac tgcccacttg gcagtacatc      240
aagtgtatca tatgccaagt acgccccta ttgacgtcaa tgacggtaaa tggcccgcct       300
ggcattatgc ccagtacatg accttatggg actttcctac ttggcagtgg tcgaggtgag      360
ccccacgttc tgcttcactc tccccatctc ccccccctcc cacccccaa ttttgtattt       420 atttattttt taattatttt gtgcagcgat ggggcgggg ggggggggg ggcgcgcgcc        480 aggcggggcg gggcggggcg aggggcgggg cggggcgagg cggagaggtg cggcggcagc      540
caatcagagc ggcgcgctcc gaaagtttcc ttttatggcg aggcggcggc ggcggcggcc      600
ctataaaaag cgaagcgcgc ggcgggcggc cgtcagatcg cctggagacg ccatccacgc      660
tgttttgacc tccatagaag acaccgggac cgatccagcc tccgcggccg ggaacggtgc      720
attggaacgc ggattcccg tgccaagagt gacgtaagta ccgcctatag agtctatagg       780 cccacccct tggcttctta tgcatgctat actgtttttg gcttggggtc tatacacccc       840
cgcttcctca tgtttgctgc ccgtgaccag cacgtcaacg attttgtggg cacgggcgac      900
accgcagtgt agtctgagca gtactcgttg ctgccgcgcg cgccaccaga cataatagct      960
gacagactaa cagactgttc ctttccatgg gtcttttctg cagtcaccgt c              1011

<210> SEQ ID NO 7
<211> LENGTH: 977
<212> TYPE: DNA
<213> ORGANISM: Artificial Sequence
<220> FEATURE:
<223> OTHER INFORMATION: Synthetic Construct

<400> SEQUENCE: 7
gacattgatt attgactagt tattaatagt aatcaattac ggggtcatta gttcatagcc       60
catatatgga gttccgcgtt acataactta cggtaaatgg cccgcctggc tgaccgccca      120 acgaccccg cccattgacg tcaataatga cgtatgttcc catagtaacg ccaataggga       180
ctttccattg acgtcaatgg gtggagtatt tacggtaaac tgcccacttg gcagtacatc      240
aagtgtatca tatgccaagt acgccccta ttgacgtcaa tgacggtaaa tggcccgcct       300
ggcattatgc ccagtacatg accttatggg actttcctac ttggcagtac atctacgtat      360
tagtcatcgc tattaccatg gtgatgcggt tttggcagta catcaatggg cgtggatagc      420
ggtttgactc acggggattt ccaagtctcc accccattga cgtcaatggg agtttgtttt      480
```

-continued

```
ggcaccaaaa tcaacgggac tttccaaaat gtcgtaacaa ctccgcccca ttgacgcaaa     540
tgggcggtag gcgtgtacgg tgggaggtct atataagcag agctcgttta gtgaaccgtc     600
agatcgcctg gagacgccat ccacgctgtt ttgacctcca tagaagacac cgggaccgat     660
ccagcctccg cggccgggaa cggtgcattg gaacgcggat tccccgtgcc aagagtgacg     720
taagtaccgc ctatagagtc tataggccca ccccttggc ttcttatgca tgctatactg      780
tttttggctt ggggtctata caccccgct tcctcatgtt tgctgcccgt gaccagcacg       840
tcaacgattt tgtgggcacg ggcgacaccg cagtgtagtc tgagcagtac tcgttgctgc     900
cgcgcgcgcc accagacata atagctgaca gactaacaga ctgttccttt ccatgggtct     960
tttctgcagt caccgtc                                                     977
```

<210> SEQ ID NO 8
<211> LENGTH: 969
<212> TYPE: DNA
<213> ORGANISM: Artificial Sequence
<220> FEATURE:
<223> OTHER INFORMATION: Synthetic Construct

<400> SEQUENCE: 8

```
gacattgatt attgactagt tattaatagt aatcaattac ggggtcatta gttcatagcc      60
catatatgga gttccgcgtt acataactta cggtaaatgg cccgcctggc tgaccgccca     120 acgaccccg cccattgacg tcaataatga cgtatgttcc catagtaacg ccaataggga      180
ctttccattg acgtcaatgg gtggagtatt tacggtaaac tgcccacttg gcagtacatc     240
aagtgtatca tatgccaagt acgccccta ttgacgtcaa tgacggtaaa tggcccgcct      300
ggcattatgc ccagtacatg accttatggg actttcctac ttggcagtac atctacgtat     360
tagtcatcgc tattaccatg tcgaggccac gttctgcttc actctcccca tctccccccc     420
ctccccaccc ccaattttgt atttatttat tttttaatta ttttgtgcag cgatggggggc     480 gggggggggg ggcgcgcgcc aggcggggcg gggcggggcg aggggcgggg cggggcgagg     540
cggagaggtg cggcggcagc caatcagagc ggcgcgctcc gaaagtttcc ttttatggcg     600
aggcggcggc ggcggcggcc ctataaaaag cgaagcgcgc ggcgggcggg agcaagcttt     660
attgcggtag tttatcacag ttaaattgct aacgcagtca gtgcttctga cacaacagtc     720
tcgaacttaa gctgcagaag ttggtcgtga ggcactgggc aggtaagtat caaggttaca     780
agacaggttt aaggagacca atagaaactg ggcttgtcga gacagagaag actcttgcgt     840
ttctgatagg cacctattgg tcttactgac atccactttg cctttctctc cacaggtgtc     900
cactcccagt tcaattacag ctcttaaggc tagagtactt aatacgactc actataggct     960
agtaatacg                                                            969
```

<210> SEQ ID NO 9
<211> LENGTH: 1678
<212> TYPE: DNA
<213> ORGANISM: Artificial Sequence
<220> FEATURE:
<223> OTHER INFORMATION: Synthetic Construct

<400> SEQUENCE: 9

```
gacattgatt attgactagt tattaatagt aatcaattac ggggtcatta gttcatagcc      60
catatatgga gttccgcgtt acataactta cggtaaatgg cccgcctggc tgaccgccca     120 acgaccccg cccattgacg tcaataatga cgtatgttcc catagtaacg ccaataggga      180
ctttccattg acgtcaatgg gtggagtatt tacggtaaac tgcccacttg gcagtacatc     240
```

-continued

```
aagtgtatca tatgccaagt acgcccccta ttgacgtcaa tgacggtaaa tggcccgcct    300
ggcattatgc ccagtacatg accttatggg actttcctac ttggcagtac atctacgtat    360
tagtcatcgc tattaccatg gtcgaggtga gccccacgtt ctgcttcact ctccccatct    420 ccccccctc cccaccccca attttgtatt tatttatttt ttaattattt tgtgcagcga    480 tggggggcggg gggggggggg gggcgcgcgc caggcggggc ggggcggggc gaggggcggg    540
gcggggcgag gcgagaggt gcggcggcag ccaatcagag cggcgcgctc cgaaagtttc    600
cttttatggc gaggcggcgg cggcggcggc cctataaaaa gcgaagcgcg cggcgggcgg    660
ggagtcgctg cgacgctgcc ttcgccccgt gccccgctcc gccgccgcct cgcgccgccc    720
gccccggctc tgactgaccg cgttactccc acaggtgagc gggcgggacg gcccttctcc    780
tccgggctgt aattagcgct tggtttaatg acggcttgtt tcttttctgt ggctgcgtga    840
aagccttgag gggctccggg agggcccttt gtgcggggggg agcggctcgg ggggtgcgtg    900
cgtgtgtgtg tgcgtgggga cgccgcgtg cggctccgcg ctgcccggcg gctgtgagcg    960
ctgcgggcgc ggcgcggggc tttgtgcgct ccgcagtgtg cgcgagggga gcgcggccgg    1020
gggcggtgcc ccgcggtgcg gggggggctg cgagggggaac aaaggctgcg tgcggggtgt    1080
gtgcgtgggg gggtgagcag ggggtgtggg cgcgtcggtc gggctgcaac ccccctgca    1140 ccccctccc cgagttgctg agcacggccc ggcttcgggt gcggggctcc gtacggggcg    1200
tggcgcgggg ctcgccgtgc cggggcgggg gtggcggcag gtggggggtgc cgggcggggc    1260 ggggccgcct cgggccgggg agggctcggg ggaggggcgc ggcggccccc ggagcgccgg    1320
cggctgtcga ggcgcggcga gccgcagcca ttgccttta tggtaatcgt gcgagagggc    1380
gcagggactt cctttgtccc aaatctgtgc ggagccgaaa tctgggaggc gccgccgcac    1440 ccctctagc gggcgcgggg cgaagcggtg cggcgccggc aggaaggaaa tgggcgggga    1500
gggccttcgt gcgtcgccgc gccgccgtcc ccttctccct ctccagcctc ggggctgtcc    1560 gcgggggac ggctgccttc ggggggggacg gggcagggcg gggttcggct tctggcgtgt    1620
gaccggcggc tctagagcct ctgctaacca tgttcatgcc ttcttctttt tcctacag     1678
```

```
<210> SEQ ID NO 10
<211> LENGTH: 323
<212> TYPE: DNA
<213> ORGANISM: Artificial Sequence
<220> FEATURE:
<223> OTHER INFORMATION: Synthetic Construct

<400> SEQUENCE: 10
cgggagcaag ctttattgcg gtagtttatc acagttaaat tgctaacgca gtcagtgctt     60
ctgacacaac agtctcgaac ttaagctgca gaagttggtc gtgaggcact gggcaggtaa    120
gtatcaaggt tacaagacag gtttaaggag accaatagaa actgggcttg tcgagacaga    180
gaagactctt gcgtttctga taggcaccta ttggtcttac tgacatccac tttgcctttc    240
tctccacagg tgtccactcc cagttcaatt acagctctta aggctagagt acttaatacg    300
actcactata ggctagtaat acg                                           323
```

```
<210> SEQ ID NO 11
<211> LENGTH: 1018
<212> TYPE: DNA
<213> ORGANISM: Artificial Sequence
<220> FEATURE:
<223> OTHER INFORMATION: Synthetic Construct
```

-continued

```
<400> SEQUENCE: 11
ggagtcgctg cgacgctgcc ttcgcccgt gccccgctcc gccgccgcct cgcgccgccc      60
gccccggctc tgactgaccg cgttactccc acaggtgagc gggcgggacg gcccttctcc     120
tccgggctgt aattagcgct tggtttaatg acggcttgtt tcttttctgt ggctgcgtga     180
aagccttgag gggctccggg agggccctt gtgcggggg agcggctcgg ggggtgcgtg      240
cgtgtgtgtg tgcgtgggga gcgccgcgtg cggctccgcg ctgcccggcg gctgtgagcg     300
ctgcgggcgc ggcgcggggc tttgtgcgct ccgcagtgtg cgcgagggga gcgcggccgg     360
gggcggtgcc ccgcggtgcg ggggggctg cgaggggaac aaaggctgcg tgcggggtgt      420
gtgcgtgggg gggtgagcag ggggtgtggg cgcgtcggtc gggctgcaac cccccctgca     480
cccccctccc cgagttgctg agcacggccc ggcttcgggt gcggggctcc gtacggggcg     540
tggcgcgggg ctcgccgtgc cgggcggggg gtggcggcag gtggggtgc cgggcggggc      600 gggccgcct cgggccgggg agggctcggg ggaggggcgc ggcggcccc ggagcgccgg       660 cggctgtcga ggcgcggcga gccgcagcca ttgcctttta tggtaatcgt gcgagagggc     720
gcagggactt cctttgtccc aaatctgtgc ggagccgaaa tctgggaggc gccgccgcac     780
cccctctagc gggcgcgggg cgaagcggtg cggcgccggc aggaaggaaa tgggcggggga    840 gggccttcgt gcgtcgccgc gccgccgtcc ccttctccct ctccagcctc ggggctgtcc     900
gcggggggac ggctgccttc ggggggacg gggcagggcg gggttcggct tctggcgtgt      960
gaccggcggc tctagagcct ctgctaacca tgttcatgcc ttcttctttt tcctacag     1018

<210> SEQ ID NO 12
<211> LENGTH: 1546
<212> TYPE: DNA
<213> ORGANISM: Artificial Sequence
<220> FEATURE:
<223> OTHER INFORMATION: Synthetic Construct

<400> SEQUENCE: 12
gacattgatt attgactagt tattaatagt aatcaattac ggggtcatta gttcatagcc      60
catatatgga gttccgcgtt acataactta cggtaaatgg cccgcctggc tgaccgccca     120
acgacccccg cccattgacg tcaataatga cgtatgttcc catagtaacg ccaatagggga    180 ctttccattg acgtcaatgg gtggagtatt tacggtaaac tgcccacttg gcagtacatc     240
aagtgtatca tatgccaagt acgccccta ttgacgtcaa tgacggtaaa tggcccgcct      300
ggcattatgc ccagtacatg accttatggg actttcctac ttggcagtac atctacgtat     360
tagtcatcgc tattaccatg gtgatgcggt tttggcagta catcaatggg cgtggatagc     420
ggtttgactc acggggattt ccaagtctcc accccattga cgtcaatggg agtttgtttt     480
ggcaccaaaa tcaacgggac tttccaaaat gtcgtaacaa ctccgcccca ttgacgcaaa     540
tgggcggtag cgtgtacgg tgggaggtct atataagcag agctcgttta gtgaaccgtc      600
agatcgcctg gagacgccat ccacgctgtt ttgacctcca tagaagacac cgggaccgat     660
ccagcctccg cggccgggaa cggtgcattg gaacgcggat tccccgtgcc aagagtgacg     720
taagtaccgc ctatagagtc tataggccca ccccccttggc ttcttatgca tgctatactg    780
tttttggctt ggggtctata cacccccgct tcctcatgtt ataggtgatg gtatagctta     840
gcctataggt gtgggttatt gaccattatt gaccactccc ctattggtga cgatactttc     900
cattactaat ccataacatg gctctttgcc acaactctct ttattggcta tatgccaata     960
cactgtcctt cagagactga cacggactct gtattttac aggatggggt ctcatttatt     1020
```

-continued

```
atttacaaat tcacatatac aacaccaccg tccccagtgc ccgcagtttt tattaaacat    1080
aacgtgggat ctccacgcga atctcgggta cgtgttccgg acatgggctc ttctccggta    1140
gcggcggagc ttctacatcc gagccctgct cccatgcctc cagcgactca tggtcgctcg    1200
gcagctcctt gctcctaaca gtggaggcca gacttaggca cagcacgatg cccaccacca    1260
ccagtgtgcc gcacaaggcc gtggcggtag ggtatgtgtc tgaaaatgag ctcggggagc    1320
gggcttgcac cgctgacgca tttggaagac ttaaggcagc ggcagaagaa gatgcaggca    1380
gctgagttgt tgtgttctga taagagtcag aggtaactcc cgttgcggtg ctgttaacgg    1440
tggagggcag tgtagtctga gcagtactcg ttgctgccgc gcgcgccacc agacataata    1500
gctgacagac taacagactg ttcctttcca tgggtctttt ctgcag                  1546
```

SYNTHETIC PROMOTERS FOR GENE THERAPY AND PROTEIN EXPRESSION

CROSS-REFERENCE TO RELATED APPLICATIONS

This application is a national phase application, filed under 35 U.S.C. § 371, of International Patent Application No. PCT/US2022/019976, filed Mar. 11, 2022, which claims the benefit of U.S. Provisional Patent Application No. 63/160,415, filed Mar. 12, 2021, which is incorporated herein by reference in its entirety.

STATEMENT AS TO FEDERALLY FUNDED RESEARCH

This invention was made with government support provided under Grant No. W911NF-13-1-0346 awarded by the Department of Defense. The U.S. government has certain rights in the invention.

SEQUENCE LISTING

The instant application contains a Sequence Listing which has been submitted electronically in ASCII format and is hereby incorporated by reference in its entirety. Said ASCII copy, created on Mar. 7, 2022, is named 50811-007WO2_Sequence_Listing_3_7_22_ST25 and is 14,738 bytes in size.

BACKGROUND OF THE INVENTION

The cytomegalovirus (CMV) promoter is used in mammalian and non-mammalian (e.g., yeast) vectors due to its compact size and relatively high transgene expression across many cell types. The native CMV gene found in many mammals, including humans, contains an intronic enhancer sequence embedded in the 5' UTR. Heterologous protein expression from the CMV promoter is significantly reduced if this intronic sequence is removed, indicating the importance of intronic elements for optimal protein expression. However, the large size of the native intronic sequence (~1 kilobase) limits its usage in many expression vectors, including gene therapy vectors. Accordingly, there exists a need for synthetic promoters (e.g., improved CMV promoters) for use in expression vectors for protein expression and gene therapy.

SUMMARY OF THE INVENTION

In one aspect, the disclosure features a promoter-associated intronic sequence comprising a nucleic acid sequence having at least 95% sequence identity to SEQ ID NO: 1.

In some aspects, the nucleic acid sequence has at least 96% sequence identity to SEQ ID NO: 1. In some aspects, the nucleic acid sequence has at least 97% sequence identity to SEQ ID NO: 1. In some aspects, the nucleic acid sequence has at least 98% sequence identity to SEQ ID NO: 1. In some aspects, the nucleic acid sequence has at least 99% sequence identity to SEQ ID NO: 1.

In another aspect, the disclosure features a promoter-associated intronic sequence comprising the nucleic acid sequence of SEQ ID NO: 1.

In another aspect, the disclosure features a promoter-associated intronic sequence consisting of the nucleic acid sequence of SEQ ID NO: 1.

In another aspect, the disclosure features a polynucleotide comprising the promoter-associated intronic sequence of any one of the above aspects and a nucleic acid sequence encoding an enhancer sequence.

In some aspects, the polynucleotide further comprises a nucleic acid sequence encoding a core promoter sequence.

In another aspect, the disclosure features a promoter sequence comprising a nucleic acid sequence comprising an enhancer sequence, a nucleic acid sequence comprising a core promoter sequence, and the promoter-associated intronic sequence of any one of the above aspects.

In some aspects, the nucleic acid sequence comprising the core promoter sequence is (a) operably linked at its 5' end to the 3' end of the enhancer sequence; and (b) operably linked at its 3' end to the 5' end of the promoter-associated intronic sequence.

In some aspects, the enhancer sequence is a CMV enhancer sequence. In some aspects, the CMV enhancer sequence comprises a nucleic acid sequence having at least 95% identity to SEQ ID NO: 3. In some aspects, the CMV enhancer sequence comprises the nucleic acid sequence of SEQ ID NO: 3. In some aspects, the CMV enhancer sequence consists of the nucleic acid sequence of SEQ ID NO: 3.

In some aspects, the core promoter sequence is a chicken β-actin core promoter sequence. In some aspects, the chicken β-actin core promoter sequence comprises a nucleic acid sequence having at least 95% identity to SEQ ID NO: 4. In some aspects, the chicken β-actin core promoter sequence comprises the nucleic acid sequence of SEQ ID NO: 4. In some aspects, the chicken β-actin core promoter sequence consists of the nucleic acid sequence of SEQ ID NO: 4.

In another aspect, the disclosure provides a promoter sequence comprising a nucleic acid sequence having at least 95% identity to SEQ ID NO: 6. In some aspects, the nucleic acid sequence has at least 96% identity to SEQ ID NO: 6. In some aspects, the nucleic acid sequence has at least 97% identity to SEQ ID NO: 6. In some aspects, the nucleic acid sequence has at least 98% identity to SEQ ID NO: 6. In some aspects, the nucleic acid sequence has at least 99% identity to SEQ ID NO: 6.

In another aspect, the disclosure features a promoter sequence comprising the nucleic acid sequence of SEQ ID NO: 6.

In another aspect, the disclosure features a promoter sequence consisting of the nucleic acid sequence of SEQ ID NO: 6.

In some aspects, the promoter sequence is operably linked to a target nucleic acid sequence.

In some aspects, the target nucleic acid sequence is operably linked at its 5' end to the 3' end of the promoter-associated intronic sequence.

In some aspects, the target nucleic acid sequence encodes an RNA. In some aspects, the RNA is a miRNA, an siRNA, a shRNA, or a guide RNA (gRNA).

In some aspects, the target nucleic acid sequence encodes an mRNA that is translated to a protein or polypeptide.

In another aspect, the disclosure features a delivery vehicle comprising the polynucleotide of either of the above two aspects.

In some aspects, the delivery vehicle is a viral vector. In some aspects, the viral vector is an adeno-associated viral (AAV) vector.

In some aspects, the delivery vehicle is a lentiviral vector.

In another aspect, the disclosure features a host cell comprising a polynucleotide of any one of the above aspects.

In another aspect, the disclosure features a host cell comprising a delivery vehicle of any one of the above aspects.

In another aspect, the disclosure features a method of producing an RNA, protein, or polypeptide in a cell, the method comprising (a) providing a polynucleotide comprising a promoter sequence of any one of the above aspects and a target nucleic acid sequence encoding the RNA, protein, or polypeptide, wherein the promoter sequence is operably linked to the target nucleic acid sequence; (b) introducing the polynucleotide into a host cell; and (c) exposing the host cell comprising the polynucleotide to conditions suitable for expression of the RNA, protein, or polypeptide, thereby producing the RNA, protein, or polypeptide.

In some aspects, the method further comprises (d) recovering the RNA, protein, or polypeptide from the host cell or host cell culture medium.

In some aspects, the polynucleotide is comprised by a delivery vehicle.

In another aspect, the disclosure features a method of expressing an RNA, protein, or polypeptide in a subject, the method comprising administering to the subject an effective amount of a delivery vehicle comprising a polynucleotide comprising a promoter sequence of any one of the above aspects and a target nucleic acid sequence encoding the RNA, protein, or polypeptide, wherein the promoter sequence is operably linked to the target nucleic acid sequence.

In another aspect, the disclosure features a method of treating a subject in need thereof, the method comprising administering to the subject an effective amount of a delivery vehicle comprising a polynucleotide comprising a promoter sequence of any one of the above aspects and a target nucleic acid sequence encoding an RNA, protein, or polypeptide, wherein the promoter sequence is operably linked to the target nucleic acid sequence, and wherein expression of the RNA, protein, or polypeptide treats a disease or disorder.

In another aspect, the disclosure features a method of inducing an immune response in a subject, the method comprising administering to the subject an effective amount of a delivery vehicle comprising a polynucleotide comprising a promoter sequence of any one of the above aspects and a target nucleic acid sequence encoding an RNA, protein, or polypeptide, wherein the promoter sequence is operably linked to the target nucleic acid sequence, and wherein expression of the RNA, protein, or polypeptide elicits an immune response.

In some aspects, the delivery vehicle is a vector. In some aspects, the vector is a viral vector. In some aspects, the viral vector is an AAV vector. In some aspects, the AAV vector is a single chain rAAV vector. In some aspects, the AAV vector is a self-complementary AAV. In some aspects, the viral vector is a lentiviral vector.

Other features and advantages of the invention will be apparent from the following description of the preferred embodiments thereof, and from the claims.

BRIEF DESCRIPTION OF THE DRAWINGS

FIG. 1A is a schematic diagram depicting the design of the synthetic promoters CB7, CB6, sCMV-CBA, and sCMV. Each promoter includes a wild-type CMV enhancer, a core promoter (chicken β-actin (CBA) core promoter or CMV core promoter), and a promoter-associated intron (chimera chicken β-actin/rabbit β-globin intron, β-globin/IgG chimeric intron, or synthetic (s) CMV intron/exon).

FIG. 1B is a schematic diagram depicting the wild-type CMV promoter.

DETAILED DESCRIPTION OF EMBODIMENTS OF THE INVENTION

I. Definitions

Figure 2:
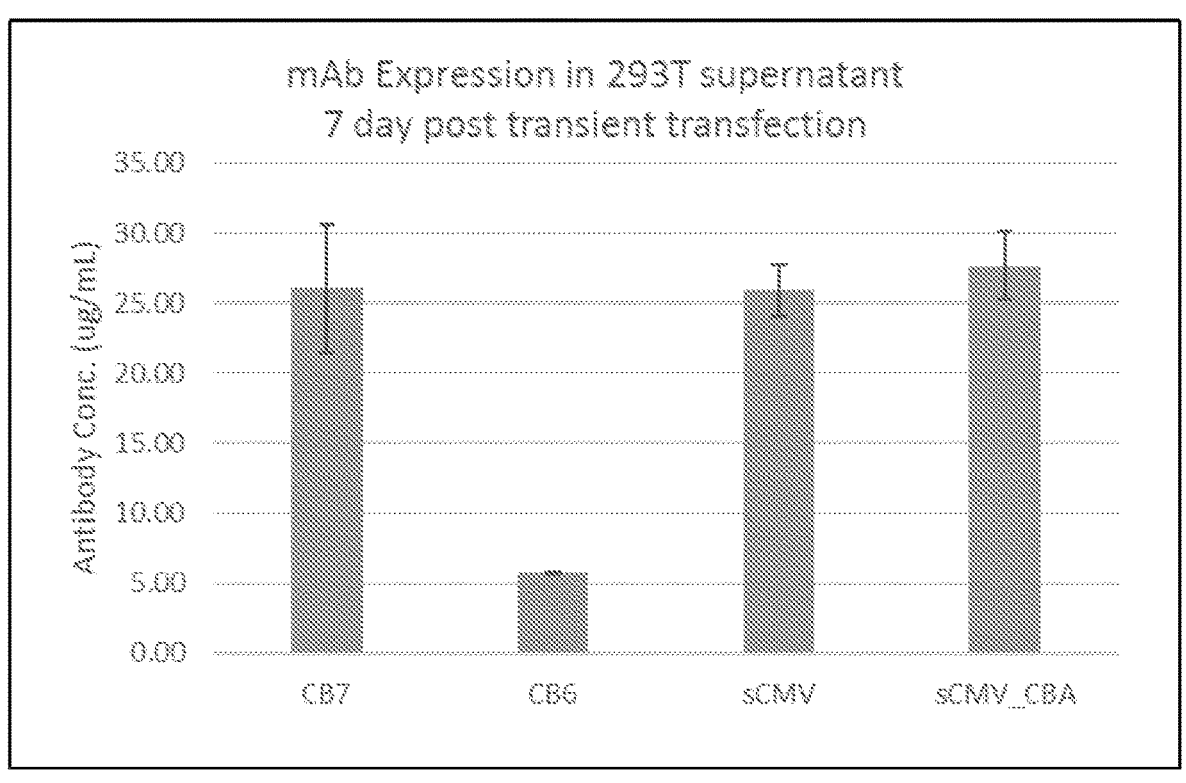
FIG. 2 is a bar graph showing the expression level of an IgG1 monoclonal antibody (mAb) in 293T cells that were transiently transfected with pAAV vector containing the IgG mAb sequence operably linked to one of four promoter sequences: CB7, CB6, sCMV, and sCMV-CBA. Error bars represent the range in antibody concentration (µg/mL) values observed in 3 replicates. These data were collected as described in Example 2.

The term "about," as used herein, refers to the usual error range for the respective value readily known to the skilled person in this technical field. Reference to "about" a value or parameter herein includes (and describes) embodiments that are directed to that value or parameter per se.

The terms "promoter" and "promoter sequence," as used herein, refer to a nucleotide sequence (e.g., a DNA sequence) that provides an initial binding site for a polymerase (e.g., an RNA polymerase) in the process of RNA transcription. A promoter may be operably linked to a target nucleic acid sequence (e.g., a target gene) that is transcribed by the polymerase. In some embodiments, the promoter is located upstream of (e.g., immediately upstream of, e.g., at the 5' end of) the transcription start site of the target nucleic acid sequence. Promoters comprise a core promoter sequence comprising one or more recognition sites (e.g., a TATA box or a B recognition element (BRE)) that are required for binding of the polymerase, but may not be sufficient to drive expression of a target nucleic acid (e.g., a target gene) in the absence of additional promoter elements. Promoters may further include regulatory nucleotide sequences involved in controlling the level of transcription of a given gene, e.g., enhancer sequences, promoter-associated intronic sequences, transcription factor binding sites, silencers, and boundary elements. Such regulatory nucleotide sequences may be located immediately adjacent to the region of the promoter comprising the core promoter sequence, or may be spatially separated from the core promoter sequence. Exemplary promoters include cytomegalovirus (CMV) promoters and synthetic promoters, e.g., synthetic promoters comprising sequences derived from CMV promoters.

As used herein, the term "core promoter" refers to a minimal nucleotide sequence (e.g., DNA sequence) that comprises one or more recognition sites (e.g., TATA box, B recognition element (BRE)) that are required for binding of a polymerase (e.g., an RNA polymerase). A core promoter sequence is required for RNA transcription. Exemplary core promoters include the chicken β-actin (CBA) core promoter (SEQ ID NO: 4) and the cytomegalovirus (CMV) core promoter (SEQ ID NO: 5).

The term "enhancer," as used herein, refers to a regulatory nucleotide sequence that can increase the level of transcription of a target nucleic acid sequence (e.g., a target gene) by a polymerase. Enhancers may be bound by proteins (e.g., transcription factors, e.g., transcriptional activators) that increase the likelihood that transcription of the target nucleic acid will occur. In some embodiments, an enhancer is located immediately adjacent to the region of the promoter comprising the core promoter sequence. In other embodiments, the enhancer is spatially separated from the core promoter sequence, e.g., upstream or downstream of the transcription start site or at a considerable distance from the region of the promoter comprising the core promoter sequence. One exemplary enhancer is the CMV enhancer.

The term "promoter-associated intronic sequence," as used herein, refers to a non-transcribed (e.g., intronic) sequence that is involved in controlling the level of transcription of a given target nucleic acid sequence (e.g., target gene). In some embodiments, the promoter-associated intronic sequence is located proximally to (e.g., downstream of) the region of the promoter comprising the core promoter sequence. One exemplary promoter-associated intronic sequence is the intronic enhancer located in the 5' UTR of the CMV gene native to mammals (e.g., humans). Heterologous protein expression from the CMV promoter is significantly reduced if this intronic sequence is removed. Further examples of promoter-associated intronic sequences include a chimera chicken β-actin/rabbit β-globin intronic sequence, a β-globin/IgG chimeric intronic sequence, and a synthetic CMV (sCMV) intron/exon (SEQ ID NO: 1).

The term "delivery vehicle" refers to a construct which is capable of delivering, and, within preferred embodiments expressing, all or a fragment of one or more gene(s) or nucleic acid molecule(s) of interest in a host cell or subject. The term "fragment of," as used herein, refers to a segment (e.g., segments of at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, at least about 97%, at least about 98%, at least about 99%, at least about 99.5%, or at least about 99.9%) of the full length gene(s) or nucleic acid molecule(s) of interest. Representative examples of such delivery vehicles include, but are not limited to, vectors, e.g., viral vectors (e.g., adeno-associated virus (AAV) expression vectors, lentiviral vectors, adenoviral vectors, vaccinia viral vectors, HSV vectors, baculoviral vectors, and retroviral vectors), and nucleic acid expression vectors. In some embodiments, the delivery vehicle includes a promoter (e.g., a synthetic promoter as described herein), wherein the promoter is operably linked to the gene(s) or nucleic acid molecule(s) of interest.

As used herein, the term "vector" is meant to include, but is not limited to, a nucleic acid molecule that is capable of transporting another nucleic acid to which it has been linked. Exemplary vectors include viral vectors (e.g., a lentivirus or an adenovirus, e.g., a recombinant adeno-associated virus (rAAV) (e.g., a single chain rAAV vector or a self-complementary AAV (scAAV) vector)), plasmids, cationic lipids (e.g., liposomes), cationic polymers (e.g., polysomes), virosomes, nanoparticles, and dentrimers. In viral vectors, additional DNA segments (e.g., synthetic promoters described herein) may be ligated into the viral genome, and the viral vector may then be administered to the subject in order to allow for transgene expression in a manner analogous to gene therapy. The term "plasmid" refers to a circular double-stranded DNA molecule into which additional DNA segments may be ligated. Certain vectors are capable of autonomous replication in a host cell into which they are introduced (e.g., bacterial vectors having a bacterial origin of replication and episomal mammalian vectors). Other vectors (e.g., non-episomal mammalian vectors) can be integrated into the genome of a host cell upon introduction into the host cell, and thereby are replicated along with the host genome. Moreover, certain vectors are capable of directing the expression of genes to which they are operably linked. Such vectors are referred to herein as "recombinant expression vectors" (or simply, "expression vectors").

A "disorder" is any condition that would benefit from treatment including, but not limited to, chronic and acute disorders or diseases, including those pathological conditions which predispose the subject (e.g., mammal) to the disorder in question.

The terms "effective amount," "effective dose," and "effective dosage," as used herein, are defined as an amount sufficient to achieve, or at least partially achieve, the desired effect. The term "therapeutically effective dose" or "therapeutically effective amount" is defined as an amount sufficient to prevent, cure, or at least partially arrest, the disease and its complications in a subject already suffering from the disease or at risk of developing the disease. Amounts effective for this use will depend upon the severity of the disorder being treated and the general state of the subject's health (e.g., immune system).

The terms "synthetic" and "engineered," as used herein, refer to a protein molecule, a nucleic acid, complex, substance, or entity that has been designed, produced, prepared, synthesized, and/or manufactured by human intervention. An engineered or synthetic product is a product that does not occur in nature.

The term "host cell," as used herein, is intended to refer to a cell into which a promoter described herein (e.g., a synthetic promoter) or a delivery vehicle comprising such a promoter has been introduced. It should be understood that such a term is intended to refer not only to the particular subject cell but to the progeny of such a cell. Because certain modifications may occur in succeeding generations due to either mutation or environmental influences, such progeny may not, in fact, be identical to the parent cell, but are still included within the scope of the term "host cell" as used herein.

The term "nucleic acid molecule" or "nucleic acid sequence," as used herein, is intended to include DNA molecules and RNA molecules. A nucleic acid molecule may be single-stranded or double-stranded, but preferably is double-stranded DNA.

The term "isolated nucleic acid," as used herein in reference to nucleic acid molecules encoding a synthetic promoter or portions thereof, is intended to refer to a nucleic acid molecule in which the nucleotide sequences encoding the synthetic promoter or portions thereof are free of other nucleotide sequences encoding a promoter other than the synthetic promoter described herein.

As used herein, the term "operably linked" refers to a first molecule that can be joined, either directly or indirectly, to a second molecule, wherein the molecules are so arranged that the first molecule affects the function of the second molecule, or vice versa. The term "operably linked" includes the juxtaposition of two or more components (e.g., a synthetic promoter and another sequence element) such that both components function normally and allow for the possibility that at least one of the components can mediate a function that is exerted upon at least one of the other components. The two molecules may or may not be adjacent or immediately adjacent. For example, a synthetic promoter is operably linked to a transcribable polynucleotide molecule if the synthetic promoter modulates transcription of the transcribable polynucleotide molecule of interest in a cell. In additional embodiments, two portions of a transcription regulatory element are operably linked to one another if they are joined such that the transcription-activating functionality of one portion is not adversely affected by the presence of the other portion. Two transcription regulatory elements may be operably linked to one another by way of a linker nucleic acid (e.g., an intervening non-coding nucleic acid) or may be operably linked to one another with no intervening nucleotides present.

"Percent (%) sequence identity" with respect to a reference polynucleotide sequence is defined as the percentage of nucleic acid residues in a candidate sequence that are identical with the nucleic acid residues in the reference polynucleotide sequence, after aligning the sequences and introducing gaps, if necessary, to achieve the maximum percent sequence identity, and not considering any conservative substitutions as part of the sequence identity. Alignment for purposes of determining percent nucleic acid sequence identity can be achieved in various ways that are within the skill in the art, for instance, using publicly available computer software such as BLAST, BLAST-2, ALIGN or Megalign (DNASTAR) software. Those skilled in the art can determine appropriate parameters for aligning sequences, including any algorithms needed to achieve maximal alignment over the full length of the sequences being compared.

For example, percent sequence identity values may be generated using the sequence comparison computer program BLAST. As an illustration, the percent sequence identity of a given nucleic acid sequence, A, to, with, or against a given nucleic acid sequence, B, (which can alternatively be phrased as a given nucleic acid sequence, A that has a certain percent sequence identity to, with, or against a given nucleic acid sequence, B) is calculated as follows:

$$100 \text{ multiplied by (the fraction } X/Y)$$

where X is the number of nucleic acids scored as identical matches by a sequence alignment program (e.g., BLAST) in that program's alignment of A and B, and where Y is the total number of nucleic acids in B. It will be appreciated that where the length of nucleic acid sequence A is not equal to the length of nucleic acid sequence B, the percent sequence identity of A to B will not equal the percent sequence identity of B to A.

The term "pharmaceutical composition" refers to a preparation which is in such form as to permit the biological activity of an active ingredient contained therein to be effective, and which contains no additional components which are unacceptably toxic to a subject to which the formulation would be administered.

A "pharmaceutically acceptable carrier" refers to an ingredient in a pharmaceutical formulation, other than an active ingredient, which is nontoxic to a subject. A pharmaceutically acceptable carrier includes, but is not limited to, a buffer, excipient, stabilizer, or preservative.

The term "polynucleotide," as used herein, refers to a polymer of nucleotides. Typically, a polynucleotide is composed of nucleosides that are naturally found in DNA or RNA (e.g., adenosine, thymidine, guanosine, cytidine, uridine, deoxyadenosine, deoxythymidine, deoxyguanosine, and deoxycytidine) joined by phosphodiester bonds. The term encompasses molecules containing nucleosides or nucleoside analogs containing chemically or biologically modified bases, modified backbones, etc., whether or not found in naturally occurring nucleic acids, and such molecules may be preferred for certain applications. Where this application refers to a polynucleotide it is understood that both DNA, RNA, and in each case both single- and double-stranded forms (and components of each single-stranded molecule) are provided. "Polynucleotide sequence" as used herein can refer to the polynucleotide material itself and/or to the sequence information (i.e., the succession of letters used as abbreviations for bases) that biochemically characterizes a specific nucleic acid. A polynucleotide sequence presented herein is presented in a 5' to 3' direction unless otherwise indicated.

The term "subject" refers to an organism, for example, a vertebrate (e.g., a mammal, bird, reptile, amphibian, or fish). In some embodiments, the subject is a human. In some embodiments, the subject is a non-human mammal (e.g., a non-human primate). In some embodiments, the subject is a sheep, a goat, a cow, a rodent, a cat, a dog, an insect (e.g., a fly), or a nematode. In some embodiments, the subject is a research animal. In some embodiments, the subject is genetically engineered, e.g., a genetically engineered non-human subject. The subject may be of either sex and at any stage of development.

As used herein, the terms "treat," "treatment," and "treating," refer to reducing or ameliorating a medical condition (e.g., a disease or disorder) and/or symptoms associated therewith. It will be appreciated that, although not precluded, treating a medical condition does not require that the disorder or symptoms associated therewith be completely eliminated. Reducing or decreasing the side effects of a medical condition, such as those described herein, or the risk or progression of the medical condition, may be relative to a subject who did not receive treatment, e.g., a control, a baseline, or a known control level or measurement. The reduction or decrease may be, e.g., by about 1%, 2%, 3%, 4%, 5%, 6%, 7%, 8%, 9%, 10%, 20%, 30%, 40%, 50%, 60%, 70%, 80%, 90%, 95%, 97%, 99%, or about 100% relative to the subject who did not receive treatment or the control, baseline, or known control level or measurement, or may be a reduction in the number of days during which the subject experiences the medical condition or associated symptoms (e.g., a reduction of 1-30 days, 2-12 months, 2-5 years, or 6-12 years). Other desirable effects of treatment may include preventing recurrence of disease, alleviation of symptoms, diminishment of any direct or indirect pathological consequences of the disease, decreasing the rate of disease progression, amelioration or palliation of the disease state, and improved prognosis. As defined herein, a therapeutically effective amount of a pharmaceutical composition of the present disclosure may be readily determined by one of ordinary skill by routine methods known in the art. Dosage regimen may be adjusted to provide the optimum therapeutic response.

II. Compositions and Methods

In one aspect, the invention is based, in part, on synthetic promoters. Synthetic promoters of the invention are useful, for example, to enhance the in vitro and/or in vivo expression of target nucleic acid sequences, e.g., in protein manufacturing systems and gene therapy vectors.

A. Synthetic Promoters

The invention provides synthetic promoters or elements thereof (e.g., synthetic promoter-associated intronic sequences and enhancer sequences) that enhance expression of target nucleic acid sequences (e.g., RNAs) or desired proteins or polypeptides translated from such nucleic acid sequences in vitro and in vivo. In some embodiments, the promoters are for use in mammalian cells or non-mammalian cells (e.g., yeast cells).

i. Promoter-Associated Intronic Sequences

In one aspect, the invention provides a promoter-associated intronic sequence having a nucleic acid sequence having at least 94% (e.g., at least 95%, 95.5%, 96%, 96.5%, 97%, 97.5%, 98%, 98.5%, 99%, 99.5%, 99.9%, or 100%, e.g., between 94% and 97%, between 95% and 99%, between 97% and 99%, or between 99% and 100%) sequence identity to SEQ ID NO: 1. In some embodiments, the nucleic acid sequence has a length of between 365 and 412 base pairs, e.g., has a length of about 365, 370, 375, 380, 385, 390, 395, 400, 405, or 410 base pairs (e.g., between 370 and 400 base pairs, between 380 and 390 base pairs, or between 385 and 390 base pairs).

In some embodiments, the nucleic acid sequence has at least 95% sequence identity to SEQ ID NO: 1. In some embodiments, the nucleic acid sequence has a length of between 369 and 408 base pairs, e.g., has a length of about 370, 375, 380, 385, 390, 395, 400, or 405 base pairs.

In some embodiments, the nucleic acid sequence has at least 96% sequence identity to SEQ ID NO: 1. In some embodiments, the nucleic acid sequence has a length of between 373 and 404 base pairs, e.g., has a length of about 375, 380, 385, 390, 395, or 400 base pairs.

In some embodiments, the nucleic acid sequence has at least 97% sequence identity to SEQ ID NO: 1. In some embodiments, the nucleic acid sequence has a length of between 377 and 400 base pairs, e.g., has a length of about 380, 385, 390, 395, or 400 base pairs.

In some embodiments, the nucleic acid sequence has at least 98% sequence identity to SEQ ID NO: 1. In some embodiments, the nucleic acid sequence has a length of between 381 and 395 base pairs, e.g., has a length of 381, 382, 383, 384, 385, 386, 387, 388, 389, 390, 391, 392, 393, 394, or 395 base pairs.

In some embodiments, the nucleic acid sequence has at least 99% sequence identity to SEQ ID NO: 1. In some embodiments, the nucleic acid sequence has a length of between 385 and 391 base pairs, e.g., has a length of 385, 386, 387, 388, 389, 390, or 391 base pairs.

In another aspect, the invention provides a promoter-associated intronic sequence comprising the nucleic acid sequence of SEQ ID NO: 1.

In another aspect, the invention provides a promoter-associated intronic sequence consisting of the nucleic acid sequence of SEQ ID NO: 1.

In some embodiments, the promoter-associated intronic sequence is operably linked to a core promoter sequence. In some embodiments, the promoter-associated intronic sequence is operably linked to one or more additional regulatory nucleotide sequences involved in controlling the level of transcription of a given gene, e.g., enhancer sequences, promoter-associated intronic sequences, transcription factor binding sites, silencers, and boundary elements. In some embodiments, the promoter-associated intronic sequence, core promoter sequence, and optionally the one or more additional regulatory nucleotide sequences are operably linked to a target nucleic acid sequence (e.g., a target gene) and promote the transcription of the target nucleic acid sequence by an RNA polymerase.

ii. Enhancer Sequences

In some aspects, the synthetic promoters described herein comprise a wild-type CMV enhancer (e.g., the wild-type 5' end of the human cytomegalovirus immediate early gene (CMV-IE-Enhancer). In some embodiments, the synthetic promoters described herein contain the sequence of SEQ ID NO: 3, or fragments or variants thereof, having at least 94% (e.g., at least 95%, 95.5%, 96%, 96.5%, 97%, 97.5%, 98%, 98.5%, 99%, 99.5%, 99.9%, or 100%) identity to SEQ ID NO: 3. In some embodiments, the synthetic promoters consist of the sequence of SEQ ID NO: 3. In some embodiments, an enhancer sequence of the synthetic promoter comprises the sequence of SEQ ID NO: 3. In some embodiments, an enhancer sequence of the synthetic promoter consists of the sequence of SEQ ID NO: 3.

In some embodiments, the enhancer sequence is operably linked to a core promoter sequence. In some embodiments, the enhancer sequence is operably linked to one or more additional regulatory nucleotide sequences involved in controlling the level of transcription of a given gene, e.g., enhancer sequences, promoter-associated intronic sequences, transcription factor binding sites, silencers, and boundary elements. In some embodiments, the enhancer sequence, core promoter sequence, and optionally the one or more additional regulatory nucleotide sequences are operably linked to a target nucleic acid sequence (e.g., a target gene) and promote the transcription of the target nucleic acid sequence by an RNA polymerase.

iii. Core Promoter Sequences

In some embodiments, the synthetic promoters described herein comprise a core promoter sequence.

In some embodiments, the synthetic promoters described herein comprise a chicken β-actin core promoter sequence. In some embodiments, the chicken β-actin core promoter sequence comprises a nucleic acid sequence having at least 94% identity to SEQ ID NO: 4 (e.g., at least 95%, 95.5%, 96%, 96.5%, 97%, 97.5%, 98%, 98.5%, 99%, 99.5%, 99.9%, or 100%, e.g., between 94% and 97%, between 95% and 99%, between 97% and 99%, or between 99% and 100% sequence identity to SEQ ID NO: 4). In some embodiments, the chicken β-actin core promoter sequence comprises of the nucleic acid sequence of SEQ ID NO: 4. In some embodiments, the chicken β-actin core promoter sequence consists of the nucleic acid sequence of SEQ ID NO: 4.

In other embodiments, the synthetic promoters described herein comprise a CMV core promoter sequence. In some embodiments, the CMV core promoter sequence comprises a nucleic acid sequence having at least 94% identity to SEQ ID NO: 5 (e.g., at least 95%, 95.5%, 96%, 96.5%, 97%, 97.5%, 98%, 98.5%, 99%, 99.5%, 99.9%, or 100%, e.g., between 94% and 97%, between 95% and 99%, between 97% and 99%, or between 99% and 100% sequence identity to SEQ ID NO: 5). In some embodiments, the CMV core promoter sequence comprises of the nucleic acid sequence of SEQ ID NO: 5. In some embodiments, the CMV core promoter sequence consists of the nucleic acid sequence of SEQ ID NO: 5.

In other embodiments, the synthetic promoters described herein comprise an EF1α, SV40, PGK, UbiC, or GRK1 core promoter sequence.

iv. Synthetic Promoters Comprising Synthetic Promoter-Associated Intronic Sequences In another aspect, the invention provides a polynucleotide comprising a promoter-associated intronic sequence as described in Section IIA(i) herein (e.g., a synthetic promoter-associated intronic sequence, e.g., a promoter-associated intronic sequence having at least 95% sequence identity to SEQ ID NO: 1) and an enhancer sequence as described in Section IIA(ii) herein (e.g., an enhancer sequence that comprises a nucleic acid sequence having at least 94% sequence identity to SEQ ID NO: 3). In some embodiments, the polynucleotide further comprises a nucleic acid sequence encoding a core promoter sequence (e.g., a core promoter sequence as described in Section IIA(iii) herein).

In another aspect, the invention provides a promoter sequence comprising a promoter-associated intronic sequence as described in Section IIA(i) herein (e.g., a synthetic promoter-associated intronic sequence, e.g., a promoter-associated intronic sequence having at least 95% sequence identity to SEQ ID NO: 1), an enhancer sequence as described in Section IIA(ii) herein (e.g., a an enhancer sequence that comprises a nucleic acid sequence having at least 94% sequence identity to SEQ ID NO: 3), and a core promoter sequence (e.g., a core promoter sequence as described in Section IIA(iii) herein). In some embodiments, the core promoter sequence is a chicken β-actin core promoter sequence comprising a nucleic acid sequence having at least 94% identity to SEQ ID NO: 4, e.g., consisting of the amino acid sequence of SEQ ID NO: 4.

In some embodiments, the nucleic acid sequence comprising the core promoter sequence is (a) operably linked at its 5' end to the 3' end of the enhancer sequence and (b) operably linked at its 3' end to the 5' end of the promoter-associated intronic sequence.

In some embodiments, the synthetic promoters described herein contain a polynucleotide of SEQ ID NO: 3 operably linked to a polynucleotide of SEQ ID NO: 1. In some embodiments, the synthetic promoters described herein contain a polynucleotide of SEQ ID NO: 3 operably linked at its 3' end to the 5' end of a polynucleotide encoding a core promoter sequence, and a polynucleotide of SEQ ID NO: 1 operably linked at its 5' end to the 3' end of the polynucleotide encoding the core promoter sequence.

In some embodiments, the synthetic promoters described herein contain a polynucleotide of SEQ ID NO: 3 operably linked to a polynucleotide of SEQ ID NO: 1. In some embodiments, the synthetic promoters described herein contain a polynucleotide of SEQ ID NO: 3 operably linked at its 3' end to the 5' end of a polynucleotide of SEQ ID NO: 4, and a polynucleotide of SEQ ID NO: 1 operably linked at its 5' end to the 3' end of the polynucleotide of SEQ ID NO: 4.

In some embodiments, the synthetic promoters described herein contain a polynucleotide of SEQ ID NO: 3 operably linked to a polynucleotide of SEQ ID NO: 1. In some embodiments, the synthetic promoters described herein contain a polynucleotide of SEQ ID NO: 3 operably linked at its 3' end to the 5' end of a polynucleotide of SEQ ID NO: 5, and a polynucleotide of SEQ ID NO: 1 operably linked at its 5' end to the 3' end of the polynucleotide of SEQ ID NO:5.

In some aspects, the invention provides a promoter sequence comprising a nucleic acid sequence having at least 94% identity to SEQ ID NO: 6 (e.g., at least 95%, 95.5%, 96%, 96.5%, 97%, 97.5%, 98%, 98.5%, 99%, 99.5%, 99.9%, or 100%, e.g., between 94% and 97%, between 95% and 99%, between 97% and 99%, or between 99% and 100% sequence identity to SEQ ID NO: 6). In some aspects, the nucleic acid sequence has at least 97% identity to SEQ ID NO: 6; at least 98% identity to SEQ ID NO: 6; or at least 99% identity to SEQ ID NO: 6.

In some aspects, the invention provides a promoter sequence comprising the nucleic acid sequence of SEQ ID NO: 6.

In some embodiments, the enhancer sequence is operably linked to one or more additional regulatory nucleotide sequences involved in controlling the level of transcription of a given gene, e.g., enhancer sequences, promoter-associated intronic sequences, transcription factor binding sites, silencers, and boundary elements.

In some aspects, the invention provides a promoter sequence consisting of the nucleic acid sequence of SEQ ID NO: 6.

In some embodiments, the enhancer sequence, core promoter sequence, and optionally the one or more additional regulatory nucleotide sequences are operably linked to a target nucleic acid sequence (e.g., a target gene) and promote the transcription of the target nucleic acid sequence by an RNA polymerase.

v. Synthetic Promoters Linked to Target Sequences

In some embodiments, a synthetic promoter as described herein is operably linked to a target nucleic acid sequence. In some embodiments, the target nucleic acid sequence is operably linked at its 5' end to the 3' end of the synthetic promoter, e.g., operably linked at its 5' end to the 3' end of the promoter-associated intronic sequence.

In some embodiments, the target nucleic acid sequence encodes an RNA that may be translated to (i.e., encodes) a protein or polypeptide of interest, e.g., a therapeutic protein or polypeptide.

In some embodiments, the target nucleic acid sequence encodes an RNA, e.g., a therapeutic RNA. In some embodiments, the RNA (e.g., therapeutic RNA) is a mRNA, a miRNA, an siRNA, a shRNA, or a guide RNA (gRNA). In some embodiments, the synthetic promoters described herein are capable of increasing expression of a target nucleic acid sequence or a protein or polypeptide encoded by such a sequence in vitro or in vivo compared to a CMV promoter or synthetic promoter of a greater length (e.g., promoters having at least 100 (e.g., at least 150, at least 175, at least 200, at least 225, at least 250, at least 275, at least 300, at least 350, at least 400, at least 450, at least 500, at least 550, at least 600, at least 650, at least 700, or more than 700) nucleic acids more than the synthetic promoter described herein)). In some embodiments, the synthetic promoters described herein are capable of increasing expression of a target nucleic acid sequence or a protein or polypeptide encoded by such a sequence in vitro or in vivo compared to the CB7 promoter (SEQ ID NO: 9). The increased expression may be relative to a promoter (e.g., a CMV promoter) that does not comprise a synthetic promoter-associated intronic sequence. For example, a polynucleotide encoding a protein of interest can be operably linked to a synthetic promoter for increased expression in vitro and improved production.

In some embodiments, the synthetic promoters described herein are capable of driving expression of a target nucleic acid sequence or a protein or polypeptide encoded by such a sequence in vitro or in vivo at a similar level as a CMV promoter or synthetic promoter of a greater length. In some embodiments, the synthetic promoters described herein are capable of driving expression of a target nucleic acid sequence or a protein or polypeptide encoded by such a sequence in vitro or in vivo at a similar level as the CB7 promoter (SEQ ID NO: 9).

In some embodiments, the synthetic promoters described herein are capable of increasing expression of a target nucleic acid sequence or a protein or polypeptide encoded by such a sequence in vitro or in vivo compared to a CMV promoter or synthetic promoter of a similar length, wherein the comparator promoter does not comprise a promoter-associated intronic sequence as described in Section IIA(i) herein (e.g., a synthetic promoter-associated intronic sequence, e.g., a promoter-associated intronic sequence having at least 95% sequence identity to SEQ ID NO: 1). In some embodiments, the synthetic promoters described herein are capable of increasing expression of a target nucleic acid sequence or a protein or polypeptide encoded by such a sequence in vitro or in vivo compared to the CB6 promoter (SEQ ID NO: 8). For example, a polynucleotide encoding a protein of interest can be operably linked to a synthetic promoter for increased expression in vitro and improved production.

In some embodiments, the synthetic promoters described herein are capable of expressing a larger protein in vitro or in vivo (e.g., are capable of expressing a large protein at a higher level) compared to a CMV promoter or synthetic promoter of a greater length (e.g., promoters having at least 100 (e.g., at least 150, at least 175, at least 200, at least 225, at least 250, at least 275, at least 300, at least 350, at least 400, at least 450, at least 500, at least 550, at least 600, at least 650, at least 700, or more than 700) nucleic acids more than the synthetic promoter described herein)).

The increased expression may be about 1.5-fold, 2-fold, 2.5-fold, 3-fold, 3.5-fold, 4-fold, 4.5-fold, 5-fold, 5.5-fold, 6-fold, 6.5-fold, 7-fold, 7.5-fold, 8-fold, 8.5-fold, 9-fold, 9.5-fold, 10-fold, 11-fold, 12-fold, 13-fold, 14-fold, 15-fold, 16-fold, 17-fold, 18-fold, 19-fold, or 20-fold, or more than 20-fold, e.g., about 1.5-fold to about 3-fold, about 3-fold to about 4.5-fold, about 4.5-fold to about 6-fold, about 6-fold to about 7.5-fold, about 7.5-fold to about 9-fold, about 9-fold to about 12-fold, about 12-fold to about 15-fold, or about 15-fold to about 20-fold relative to a comparator promoter. In some aspects, expression is increased about 5-fold relative to a comparator promoter.

In some embodiments, the synthetic promoters described herein contain the sequence of any one of SEQ ID NOs: 1-12, or fragments or variants thereof, having at least 94% (e.g., at least 95%, 95.5%, 96%, 96.5%, 97%, 97.5%, 98%, 98.5%, 99%, 99.5%, 99.9%, or 100%) sequence identity thereto.

B. Expression Vectors for Protein Production

Also featured are expression vectors containing at least one polynucleotide encoding a synthetic promoter of the invention. For example, an expression vector includes a polynucleotide comprising a synthetic promoter of the invention and variants thereof having at least 94% sequence identity thereto. Furthermore, an expression vector can include polynucleotides encoding a peptide, protein, or therapeutic agent. In some instances, the polynucleotide encoding the synthetic promoter is operably linked to the polynucleotide encoding the peptide, protein, or therapeutic agent.

In one aspect, the invention features a method of producing an RNA, protein, or polypeptide in a cell (either in vitro or in vivo), the method comprising (a) providing a polynucleotide comprising a synthetic promoter sequence as described herein and a target nucleic acid sequence encoding the RNA, protein, or polypeptide, wherein the promoter sequence is operably linked to the target nucleic acid sequence; (b) introducing the polynucleotide into a host cell; and (c) exposing the host cell comprising the polynucleotide to conditions suitable for expression of the RNA, protein, or polypeptide, thereby producing the RNA, protein, or polypeptide. In some aspects, the method further comprises (d) recovering the RNA, protein, or polypeptide from the host cell or host cell culture medium.

Expression vectors are well known in the art and include, but are not limited, to viral vectors and plasmids. Viral-based vectors for delivery of a desired polynucleotide and expression in a desired cell are well known in the art. Exemplary viral-based vehicles include, but are not limited to, recombinant retroviruses (see, e.g., PCT Publication Nos. WO 90/07936; WO 94/03622; WO 93/25698; WO 93/25234; WO 93/11230; WO 93/10218; WO 91/02805; U.S. Pat. Nos. 5,219,740 and 4,777,127), adenovirus vectors, alphavirus-based vectors (e.g., Sindbis virus vectors, Semliki forest virus), Ross River virus, adeno-associated virus (AAV) vectors (see, e.g., PCT Publication Nos. WO 94/12649, WO 93/03769; WO 93/19191; WO 94/28938; WO 95/11984 and WO 95/00655), vaccinia virus (e.g., Modified Vaccinia virus Ankara (MVA) or fowlpox), Baculovirus recombinant system, and herpes virus vectors. In some embodiments, the expression vector is a single chain rAAV vector or a self-complementary AAV (scAAV).

Nonviral vectors, such as plasmids, are also well known in the art and include, but are not limited to, prokaryotic and eukaryotic vectors (e.g., yeast- and bacteria-based plasmids), as well as plasmids for expression in mammalian cells.

Methods of introducing vectors into a host cell and isolating and purifying an expressed protein are also well known in the art (e.g., *Molecular Cloning: A Laboratory Manual*, second edition, Sambrook, et al., 1989, Cold Spring Harbor Press). Examples of host cells include, but are not limited to, mammalian cells, such as NS0, CHO cells, HEK and COS and non-mammalian cells, e.g., yeast cells.

The vector may further include a polynucleotide sequence encoding a linker sequence. Generally, the linking sequence is positioned in the vector between the polynucleotide encoding the synthetic promoter and the polynucleotide encoding the peptide, protein, or therapeutic agent. Linking sequences can encode random nucleic acid sequence or can contain functional sites.

By way of example, and not limitation, a peptide, protein, or therapeutic agent may be generated as described herein using mammalian expression vectors in mammalian cell culture systems.

The expression vectors including a synthetic promoter described herein may be used for the expression and/or production of a peptide or a protein (e.g., a therapeutic peptide or protein).

In some instances, the therapeutic peptide or protein is an antibody (e.g., Adalimumab (AMJEVITA®), Bezlotoxumab (ZINPLAVA™), Avelumab (BAVENCIO®), Dupilumab (DUPIXENT®), Durvalumab (IMFINZI®), Ocrelizumab (OCREVUS™), Brodalumab (SILIQ™), Reslizumab (CINQAIR™), Olaratumab (LARTRUVO®), Daratumumab (DARZALEX®), Elotuzumab (EMPLICITI™), Necitumumab (PORTRAZZA™), Infliximab (INFLEC-TRA®), Obiltoxaximab (ANTHIM®), Atezolizumab (TECENTRIQ®), Secukinumab (COSENTYX™), Mepolizumab (NUCALA®), Nivolumab (OPDIVO®), Alirocumab (PRALUENT®), Idarucizumab (PRAXBIND®), Evolocumab (REPATHA®), Dinutuximab (UNITUXIN™), Bevacizumab (BLINCYTO®), Pembrolizumab (KEYTRUDA®), Ramucirumab (CYRAMZA®), Vedolizumab (ENTYVIO®), Siltuximab (SYLVANT®), Alemtuzumab (LEMTRADA®), Trastuzumab emtansine (KADCYLA®), Pertuzumab (PERJETA®), Infliximab (REMSIMA®)), Obinutuzumab (GAZYVARO®), Brentuximab (ADCETRIS®), Raxibacumab (ABTHRAX®), Belimumab (BENLYSTA®), Ipilimumab (VERVOY®), Denosumab (XGEVA®), Denosumab (PROLIA®), Ofatumumab (ARZERRA®), Besilesomab (SCINTIMUN®), Tocilizumab (ROACTEMRA®), Canakinumab KARI)), Golimumab (SIMPONI®), Ustekinumab (STELARA®), Certolizumab pegol (CIMZIA®), Catumaxomab (REMOVAB®), Eculizumab (SOLIRIS®), Ranibizumab (LUCENTIS®), Panitumumab (VECTIBIX®), Natalizumab (TYSABRI®), Catumaxomab (PROXINIUM®), Bevacizumab (AVASTIN®), Omalizumab (XOLAIR®)), Cetuximab (ERBITUX®), Efalizumab (RAPTIVA®), Ibritumomab tiuxetan (ZEVALIN®), Fanolesomab (NEUTROSPEC®), Adalimumab (HUMIRA®), Tositumomab and iodine 131 tositumomab (BEXXAR®), Alemtuzumab (CAMPATH®), Trastuzumab (HERCEPTIN®), Gemtuzumab ozogamicin (MYLOTARG®), Infliximab (REMICADE®), Palivizumab (SYNAGIS®), SYNAGIS®), Necitumumab (DACLIZUMAB), Basiliximab (SIMULECT®), Rituximab (RITUXAN®), Votumumab (HUMASPECT®), Sulesomab (LEUKOSCAN®), Arcitumomab (CEA-SCAN®), Imiciromab (MYOSCINT®), Capromab (PROSTASCINT®), Nofetumomab (VERLUMA®), Abciximab (REOPRO®), Satumomab (ONCOSCINT®), or Muromonab-CD3 (ORTHOCLONE OKT3®).

In some instances, the therapeutic peptide or protein is an antibody fragment, e.g., a bis-Fab, an Fv, a Fab, a Fab'-SH, a F(ab')₂, a diabody, a linear antibody, an scFv, an scFab, a VH domain, or a VHH domain. In some instances, the therapeutic peptide or protein is a nanobody.

In some instances, the synthetic promoter can be used in the production of a therapeutic protein, a pre-pro-protein, a pro-protein, a precursor, a fragment, or derivative thereof, such as Abarelix, Abatacept, Abciximab, Adalimumab, Aflibercept, Agalsidase beta, Albiglutide, Aldesleukin, Alefacept, Alemtuzumab, Alglucerase, Alglucosidase alfa, Alirocumab, Aliskiren, Alpha-1-proteinase inhibitor, Alteplase, Anakinra, Ancestim, Anistreplase, Anthrax immune globulin human, Antihemophilic Factor, Anti-inhibitor coagulant complex, Antithrombin Alfa, Antithrombin III human, Antithymocyte globulin, Anti-thymocyte Globulin (Equine), Anti-thymocyte Globulin, Aprotinin, Arcitumomab, Asfotase Alfa, Asparaginase, Asparaginase *Erwinia chrysanthemi*, Atezolizumab, Basiliximab, Becaplermin, Belatacept, Belimumab, Beractant, Bevacizumab, Bivalirudin, Blinatumomab, Botulinum Toxin Type A, Botulinum Toxin Type B, Brentuximab vedotin, Brodalumab, Buserelin, C1 Esterase Inhibitor, Canakinumab, Canakinumab, Capromab, Certolizumab pegol, Cetuximab, Choriogonadotropin alfa, Chorionic Gonadotropin, Coagulation factor ix, Coagulation factor VIIa, Coagulation factor X human, Coagulation Factor XIII A-Subunit, Collagenase, Conestat alfa, Corticotropin, Cosyntropin, Daclizumab, Daptomycin, Daratumumab, Darbepoetin alfa, Defibrotide, Denileukin diftitox, Denosumab, Desirudin, Digoxin Immune Fab (Ovine), Dinutuximab, Dornase alfa, Drotrecogin alfa, Dulaglutide, Eculizumab, Efalizumab, Efmoroctocog alfa, Elosulfase alfa, Elotuzumab, Enfuvirtide, Epoetin alfa, Epoetin zeta, Eptifibatide, Etanercept, Evolocumab, Exenatide, Factor IX Complex, Fibrinogen Concentrate, Fibrinolysin, Filgrastim, Filgrastim-sndz, Follitropin alpha, Follitropin beta, Galsulfase, Gastric intrinsic factor, Gemtuzumab ozogamicin, Glatiramer acetate, Glucagon recombinant, Glucarpidase, Golimumab, Gramicidin D, Hepatitis A Vaccine, Hepatitis B immune globulin, Human calcitonin, Human *Clostridium tetani* toxoid immune globulin, Human rabies virus immune globulin, Human Rho(D) immune globulin, Human Serum Albumin, Human Varicella-Zoster Immune Globulin, Hyaluronidase, Ibritumomab, Ibritumomab tiuxetan, Idarucizumab, Idursulfase, Imiglucerase, Immune Globulin Human, Infliximab, Insulin aspart, Insulin Beef, Insulin Degludec, Insulin detemir, Insulin Glargine, Insulin glulisine, Insulin Lispro, Insulin Pork, Insulin Regular, Insulin porcine, Insulin isophane, Interferon Alfa-2a, Interferon alfacon-1, Interferon alfa-n1, Interferon alfa-n3, Interferon beta-1a, Interferon beta-1b, Interferon gamma-1b, Ipilimumab, Ixekizumab, Laronidase, Lenograstim, Lepirudin, Leuprolide, Liraglutide, Lucinactant, Lutropin alfa, Mecasermin, Menotropins, Mepolizumab, Methoxy polyethylene glycol-epoetin beta, Metreleptin, Muromonab, Natalizumab, Natural alpha interferon OR multiferon, Necitumumab, Nesiritide, Nivolumab, Obiltoxaximab, Obinutuzumab, Ocriplasmin, Ofatumumab, Omalizumab, Oprelvekin, OspA lipoprotein, Oxytocin, Palifermin, Palivizumab, Pancrelipase, Panitumumab, Pegademase bovine, Pegaptanib, Pegaspargase, Pegfilgrastim, Peginterferon alfa-2a, Peginterferon alfa-2b, Peginterferon beta-1a, Peglotipase, Pegvisomant, Pembrolizumab, Pertuzumab, Poractant alfa, Pramlintide, Preotact, Protamine sulfate, Protein S human, Prothrombin complex concentrate, Ramucirumab, Ranibizumab, Rasburicase, Raxibacumab, Reteplase, Rilonacept, Rituximab, Romiplostim, Sacrosidase, Salmon Calcitonin, Sargramostim, Satumomab Pendetide, Sebelipase alfa, Secretin, Secukinumab, Sermorelin, Serum albumin, Serum albumin iodonated, Siltuximab, Simoctocog Alfa, Sipuleucel-T, Somatotropin Recombinant, Somatropin recombinant, Streptokinase, Sulodexide, Susoctocog alfa, Taliglucerase alfa, Teduglutide, Teicoplanin, Tenecteplase, Teriparatide, Tesamorelin, Thrombomodulin Alfa, Thymalfasin, Thyroglobulin, Thyrotropin Alfa, Tocilizumab, Tositumomab, Trastuzumab, Tuberculin Purified Protein Derivative, Turoctocog alfa, Urofollitropin, Urokinase, Ustekinumab, Vasopressin, Vedolizumab, or Velaglucerase alfa.

For recombinant production, one or more polynucleotides encoding one or more polypeptides of interest, or any fragment or variant or derivative thereof, can be inserted into one or more expression vectors containing the synthetic promoter of the invention for further cloning and/or expression in a host cell (e.g., inserted such that the polynucleotide encoding one or more polypeptides of interest is operably linked to the synthetic promoter of the invention (e.g., immediately downstream of the synthetic promoter)). Such polynucleotides may be readily isolated and sequenced using conventional procedures. For expression, a vector (e.g., an expression vector) containing the synthetic promoter of the invention operably linked to one or more of the polynucleotides encoding one or more polypeptides of interest is provided. Methods which are well known to those skilled in the art can be used to construct expression vectors containing the synthetic promoter or any fragment or variant or derivative thereof, along with appropriate transcriptional/translational control signals and one or more polynucleotides encoding one or more polypeptides of interest. These methods include in vitro recombinant DNA techniques, synthetic techniques, and in vivo recombination/genetic recombination. See, for example, the techniques described in Maniatis et al., *Molecular Cloning: A Laboratory Manual*, Cold Spring Harbor Laboratory, N.Y. (1989); and Ausubel et al., Current Protocols in Molecular Biology, Greene Publishing Associates and Wiley Interscience, N.Y. (1989). The expression vector can be part of a plasmid, virus, or can be a nucleic acid fragment. The expression vector includes an expression cassette containing the synthetic promoter of the invention, into which the polynucleotide encoding the polypeptide of interest, or any fragment or variant or derivative thereof, is cloned into operable association with the synthetic promoter and or other transcription control elements. Two or more coding regions can be present in a single polynucleotide construct, e.g., in a single expression vector, or in separate polynucleotide constructs, e.g., in separate (different) expression vectors. Furthermore, any expression vector may contain a single coding region, or can have two or more coding regions, e.g., an expression vector described herein can encode one or more polypeptides, which are post- or co-translationally separated into the final polypeptide via proteolytic cleavage. In addition, a vector, polynucleotide, or nucleic acid described herein can contain heterologous coding regions, either fused or unfused to a polynucleotide encoding the polypeptide of interest, or any fragment or variant or derivative thereof. Heterologous coding regions include, for example, specialized elements or motifs, such as a secretory signal peptide or heterologous functional domain. An operable association is when a coding region for a gene product, (e.g., a polypeptide), is associated with one or more regulatory sequences in such a way as to place expression of the gene product under the influence or control of the regulatory sequence(s). Two DNA fragments (such as a polypeptide coding region and a synthetic promoter associated therewith) are "operably linked" if induction of the synthetic promoter function results in the transcription of mRNA encoding the desired gene product and if the nature of the linkage between the two DNA fragments does not interfere with the ability of the expression regulatory sequences to direct the expression of the gene product or interfere with the ability of the DNA template to be transcribed. Thus, the synthetic promoter region would be operably associated with a nucleic acid encoding a polypeptide if the synthetic promoter was capable of effecting transcription of that polynucleic acid. Other transcription control elements besides a promoter, for example, enhancers, operators, repressors, and transcription termination signals, can be operably associated with the polynucleotide to direct cell-specific transcription. A variety of transcription control regions are known to those skilled in the art. The expression cassette may also include other features such as an origin of replication, and/or chromosome integration elements such as retroviral long terminal repeats (LTRs), or adeno-associated viral (AAV) inverted terminal repeats (ITRs).

Once a polypeptide of interest, or a fragment thereof, has been produced by recombinant expression, it can be purified by any method known in the art for purification of a peptide molecule, for example, by chromatography (e.g., ion exchange, affinity, and sizing column chromatography), centrifugation, differential solubility, or by any other standard technique for the purification of proteins. Further, the polypeptide of interest, or any fragments thereof can be fused to heterologous polypeptide sequences described herein or otherwise known in the art to facilitate purification or to produce therapeutic peptides.

Once isolated, a polypeptide of interest, or any fragments thereof can, if desired, be further purified, e.g., by high performance liquid chromatography (see, e.g., Fisher, Laboratory Techniques in Biochemistry and Molecular Biology (Work and Burdon, eds., Elsevier, 1980); the disclosure of which is incorporated herein by reference), or by gel filtration chromatography, such as on a SUPERDEX™ 75 column (Pharmacia Biotech AB, Uppsala, Sweden).

In some embodiments, the synthetic promoters described herein are capable of increasing the yield (e.g., in vitro or in vivo yield) of a protein or polypeptide encoded by a target sequence compared to a CMV promoter or synthetic promoter of a greater length (e.g., promoters having at least 100 (e.g., at least 150, at least 175, at least 200, at least 225, at least 250, at least 275, at least 300, at least 350, at least 400, at least 450, at least 500, at least 550, at least 600, at least 650, at least 700, or more than 700) nucleic acids more than the synthetic promoter described herein)). In some embodiments, the synthetic promoters described herein are capable of increasing yield of a protein or polypeptide compared to the CB7 promoter (SEQ ID NO: 9).

In some embodiments, the synthetic promoters described herein are capable of increasing yield of a protein or polypeptide encoded by a target sequence compared to a CMV promoter or synthetic promoter of a similar length, wherein the comparator promoter does not comprise a promoter-associated intronic sequence as described in Section IIA(i) herein (e.g., a synthetic promoter-associated intronic sequence, e.g., a promoter-associated intronic sequence having at least 95% sequence identity to SEQ ID NO: 1).

The increase in protein yield may be about 1.5-fold, 2-fold, 2.5-fold, 3-fold, 3.5-fold, 4-fold, 4.5-fold, 5-fold, 5.5-fold, 6-fold, 6.5-fold, 7-fold, 7.5-fold, 8-fold, 8.5-fold, 9-fold, 9.5-fold, 10-fold, 11-fold, 12-fold, 13-fold, 14-fold, 15-fold, 16-fold, 17-fold, 18-fold, 19-fold, or 20-fold, or more than 20-fold, e.g., about 1.5-fold to about 3-fold, about 3-fold to about 4.5-fold, about 4.5-fold to about 6-fold, about 6-fold to about 7.5-fold, about 7.5-fold to about 9-fold, about 9-fold to about 12-fold, about 12-fold to about 15-fold, or about 15-fold to about 20-fold relative to a comparator promoter. In some aspects, protein yield is increased about 5-fold relative to a comparator promoter.

In some embodiments, the synthetic promoters described herein are capable of driving the production of an amount of a protein or polypeptide encoded by a target sequence in vitro or in vivo that is similar to an amount yielded by a CMV promoter or synthetic promoter of a greater length. In some embodiments, the synthetic promoters described herein are capable of driving the production of an amount of a protein or polypeptide encoded by a target sequence in vitro or in vivo that is similar to an amount yielded by the CB7 promoter (SEQ ID NO: 9).

C. Expression Vectors for Nucleic Acid Production

Also featured herein are expression vectors containing at least one polynucleotide encoding a synthetic promoter of the invention (e.g., expression vectors including a poly-nucleotide comprising a synthetic promoter of the invention and variants thereof having at least 94% sequence identity thereto) and further including a polynucleotides encoding an RNA (e.g., a therapeutic RNA, e.g., a mRNA, a miRNA, an siRNA, a shRNA, or a gRNA. In some instances, the polynucleotide encoding the synthetic promoter is operably linked to the polynucleotide encoding RNA (e.g., therapeu-tic RNA).

The vector may further include a polynucleotide sequence encoding a linker sequence. Generally, the linking sequence is positioned in the vector between the polynucleotide encoding the synthetic promoter and the polynucleotide encoding the RNA (e.g., therapeutic RNA). Linking sequences can encode random nucleic acid sequence or can contain functional sites.

By way of example, and not limitation, an RNA (e.g., a therapeutic RNA, e.g., a mRNA, a miRNA, an siRNA, a shRNA, or a guide RNA (gRNA) may be generated as described herein using mammalian expression vectors in mammalian cell culture systems.

The expression vectors including a synthetic promoter described herein may be used for the expression and/or production of an RNA (e.g., a therapeutic RNA, e.g., a mRNA, a miRNA, an siRNA, a shRNA, or a gRNA.

For recombinant production, one or more polynucleotides encoding one or more RNAs of interest, or any fragment or variant or derivative thereof, can be inserted into one or more expression vectors containing the synthetic promoter of the invention for further cloning and/or expression in a host cell (e.g., inserted such that the polynucleotide encod-ing one or more RNAs of interest is operably linked to the synthetic promoter of the invention (e.g., immediately downstream of the synthetic promoter)). Such polynucle-otides may be readily isolated and sequenced using conven-tional procedures. For expression, a vector (e.g., an expres-sion vector) containing the synthetic promoter of the invention operably linked to one or more of the polynucle-otides encoding one or more RNAs of interest is provided. Methods which are well known to those skilled in the art can be used to construct expression vectors containing the synthetic promoter or any fragment or variant or derivative thereof, along with appropriate transcriptional/translational control signals and one or more polynucleotides encoding one or more RNAs of interest. These methods include in vitro recombinant DNA techniques, synthetic techniques, and in vivo recombination/genetic recombination. See, for example, the techniques described in Maniatis et al., *Molecular Cloning: A Laboratory Manual*, Cold Spring Harbor Laboratory, N.Y. (1989); and Ausubel et al., Current Protocols in Molecular Biology, Greene Publishing Associ-ates and Wiley Interscience, N.Y. (1989). The expression vector can be part of a plasmid, virus, or can be a nucleic acid fragment. The expression vector includes an expression cassette containing the synthetic promoter of the invention, into which the polynucleotide encoding the RNA of interest, or any fragment or variant or derivative thereof, is cloned into operable association with the synthetic promoter and or other transcription control elements.

In some embodiments, the synthetic promoters described herein are capable of increasing the yield (e.g., in vitro or in vivo yield) of an RNA encoded by a target sequence compared to a CMV promoter or synthetic promoter of a greater length (e.g., promoters having at least 100 (e.g., at least 150, at least 175, at least 200, at least 225, at least 250, at least 275, at least 300, at least 350, at least 400, at least 450, at least 500, at least 550, at least 600, at least 650, at least 700, or more than 700) nucleic acids more than the synthetic promoter described herein)). In some embodi-ments, the synthetic promoters described herein are capable of increasing yield of an RNA compared to the CB7 pro-moter (SEQ ID NO: 9).

In some embodiments, the synthetic promoters described herein are capable of increasing yield of an RNA encoded by a target sequence compared to a CMV promoter or synthetic promoter of a similar length, wherein the comparator pro-moter does not comprise a promoter-associated intronic sequence as described in Section IIA(i) herein (e.g., a synthetic promoter-associated intronic sequence, e.g., a pro-moter-associated intronic sequence having at least 95% sequence identity to SEQ ID NO: 1).

The increase in RNA yield may be about 1.5-fold, 2-fold, 2.5-fold, 3-fold, 3.5-fold, 4-fold, 4.5-fold, 5-fold, 5.5-fold, 6-fold, 6.5-fold, 7-fold, 7.5-fold, 8-fold, 8.5-fold, 9-fold, 9.5-fold, 10-fold, 11-fold, 12-fold, 13-fold, 14-fold, 15-fold, 16-fold, 17-fold, 18-fold, 19-fold, or 20-fold, or more than 20-fold, e.g., about 1.5-fold to about 3-fold, about 3-fold to about 4.5-fold, about 4.5-fold to about 6-fold, about 6-fold to about 7.5-fold, about 7.5-fold to about 9-fold, about 9-fold to about 12-fold, about 12-fold to about 15-fold, or about 15-fold to about 20-fold relative to a comparator promoter. In some aspects, RNA yield is increased about 5-fold relative to a comparator promoter.

In some embodiments, the synthetic promoters described herein are capable of driving the production of an amount of an RNA encoded by a target sequence in vitro or in vivo that is similar to an amount yielded by a CMV promoter or synthetic promoter of a greater length. In some embodi-ments, the synthetic promoters described herein are capable of driving the production of an amount of an RNA encoded by a target sequence in vitro or in vivo that is similar to an amount yielded by the CB7 promoter (SEQ ID NO: 9).

D. Pharmaceutical Compositions

In another aspect, the present invention provides a com-position, e.g., a pharmaceutical composition or delivery vehicle (e.g., a viral vector (e.g., adenoviral, AAV (e.g., rAAV), lentivirus (e.g., lentivirus GOI), vaccinia viral, HSV, or baculoviral vector) containing one or more (e.g., 1, 2, 3, or 4 or more) of the synthetic promoters of the present invention. The pharmaceutical compositions may be formu-lated together with a pharmaceutically acceptable carrier, excipient, or diluent. In some instances, the composition comprises a set of viral vectors containing a synthetic promoter of the present invention, wherein each member of the set includes a different target nucleic acid molecule having a nucleic acid sequence encoding a different RNA, protein, or polypeptide of interest.

A pharmaceutical composition of the present invention can be administered by a variety of methods known in the art. As will be appreciated by the skilled artisan, the route and/or mode of administration will vary depending upon the desired results. The active compounds can be prepared with carriers that will protect the compound against rapid release, such as a controlled release formulation, including implants, transdermal patches, and microencapsulated delivery systems. Biodegradable, biocompatible polymers can be used, such as ethylene vinyl acetate, polyanhydrides, polyglycolic acid, collagen, polyorthoesters, and polylactic acid. Many methods for the preparation of such formulations are patented or generally known to those skilled in the art.

To administer a compound of the invention by certain routes of administration, it may be necessary to coat the compound with, or co-administer the compound with, a material to prevent its inactivation. For example, the compound may be administered to a subject in an appropriate carrier, for example, liposomes, or in a diluent. Pharmaceutically acceptable diluents include saline and aqueous buffer solutions. Liposomes include water-in-oil-in-water CGF emulsions as well as conventional liposomes.

Pharmaceutically acceptable carriers include sterile aqueous solutions or dispersions and sterile powders for the extemporaneous preparation of sterile injectable solutions or dispersion. The use of such media and agents for pharmaceutically active substances is known in the art. Except insofar as any conventional media or agent is incompatible with the active compound, use thereof in the pharmaceutical compositions of the invention is contemplated. Supplementary active compounds can also be incorporated into the compositions.

Pharmaceutical compositions of the invention also can be administered in combination therapy, i.e., combined with other agents. For example, the combination therapy can include a composition of the present invention with at least one or more additional therapeutic agents as necessary for the particular indication (e.g., a disease or disorder described herein) being treated.

Active ingredients may be entrapped in microcapsules prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nano-particles and nanocapsules) or in macroemulsions.

The formulations to be used for in vivo administration are generally sterile. Sterility may be readily accomplished, e.g., by filtration through sterile filtration membranes. Sterile injectable solutions can be prepared by incorporating the active compound in the required amount in an appropriate solvent with one or a combination of ingredients enumerated above, as required, followed by sterilization microfiltration. Generally, dispersions are prepared by incorporating the active compound into a sterile vehicle that contains a basic dispersion medium and the required other ingredients from those enumerated above. In the case of sterile powders for the preparation of sterile injectable solutions, the preferred methods of preparation are vacuum drying and freeze-drying (lyophilization) that yield a powder of the active ingredient plus any additional desired ingredient from a previously sterile-filtered solution thereof. Therapeutic compositions typically must be sterile and stable under the conditions of manufacture and storage. The composition can be formulated as a solution, microemulsion, liposome, or other ordered structure suitable to high drug concentration. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants, such as TWEEN® 80. In many cases, it will be preferable to include isotonic agents, for example, sugars, polyalcohols such as mannitol, sorbitol, or sodium chloride in the composition. Prolonged absorption of the injectable compositions can be brought about by including in the composition an agent that delays absorption, for example, monostearate salts and gelatin.

Alternatively, delivery vehicles (e.g., viral vectors having a synthetic promoter of the invention) may be delivered directly into the subject for expression. For example, delivery vehicles (e.g., viral vectors, such as recombinant viruses), can be used to deliver a gene therapy introducing a beneficial RNA, protein, or polypeptide to a subject having a mutated, absent, or non-functional version of the RNA, protein, or polypeptide or to a subject having a working version of the RNA, protein or polypeptide. In another embodiment, delivery vehicles can be used to deliver a gene encoding all or a portion of an antibody (e.g., the heavy and light chain of an antibody). In one example, rAAV virus particles can be used to deliver anti-HIV monoclonal antibodies (Balazs et al. *Nature.* 481: 81, 2012). Antibody genes could also be effectively delivered by electroporation of muscle cells with plasmid DNA containing heavy and/or light chain genes (e.g., VH and/or VL genes) (Muthumani et al. *Hum Vaccin Immunother.* 10: 2253, 2013). Lentivirus vectors or other nucleic acids (e.g., RNA) capable of delivering transgenes could also be used to deliver antibody genes to establish serum antibody levels capable of prevention.

Also within the scope of the present invention are kits including synthetic promoters of the invention and, optionally, instructions for use. The kits can further contain one or more additional reagents, such as a second, different synthetic promoter that is operably linked to a different polynucleotide encoding the same of a different polypeptide of interest.

In another aspect of the invention, an article of manufacture containing materials (e.g., pharmaceutical compositions described above) useful for the treatment, prevention and/or diagnosis of the disorders described herein is provided. The article of manufacture comprises a container and a label or package insert on or associated with the container. Suitable containers include, for example, bottles, vials, syringes, IV solution bags, etc. The containers may be formed from a variety of materials such as glass or plastic. The container holds a composition which is by itself or combined with another composition effective for treating, preventing and/or diagnosing the condition and may have a sterile access port (for example the container may be an intravenous solution bag or a vial having a stopper pierceable by a hypodermic injection needle). At least one active agent in the composition is a delivery vehicle (e.g., a viral vector) containing a therapeutic gene, the expression of which is driven by a synthetic promoter described herein. The label or package insert indicates that the composition is used for treating the condition of choice. Moreover, the article of manufacture may comprise (a) a first container with a composition contained therein, wherein the composition comprises a delivery vehicle (e.g., a viral vector) containing a therapeutic gene, the expression of which is driven by a synthetic promoter described herein; and (b) a second container with a composition contained therein, wherein the composition comprises a further cytotoxic or otherwise therapeutic agent.

The article of manufacture in this embodiment of the invention may further comprise a package insert indicating that the compositions can be used to treat a particular condition. In some embodiments, the invention provides a kit comprising a modified delivery vehicle (e.g., a viral vector) containing a therapeutic gene, the expression of which is driven by a synthetic promoter described herein and a package insert with instructions for using the delivery vehicle for treating a subject having or at risk of developing a disorder associated with a genetic mutation. Alternatively, or additionally, the article of manufacture may further comprise a second (or third) container comprising a pharmaceutically acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

E. Treatment of a Disease

The compositions described herein can be used in methods of treating various diseases or disorders (e.g., a disease or disorder listed in Table 1). In some instances, the synthetic promoters may be incorporated in a delivery vehicle (e.g., a vector (e.g., a viral vector (e.g., an adenoviral, AAV, vaccinia viral, HSV, or baculoviral vector))) and operably linked to a target nucleic acid sequence encoding a target nucleic acid sequence (e.g., an RNA) or a desired protein or polypeptide translated from such a nucleic acid sequence. In some embodiments, the methods described herein relate to treating a subject having a disease or disorder listed in Table 1. For example, the methods may comprise using a delivery vehicle comprising a synthetic promoter to deliver a gene therapy introducing a beneficial RNA, protein, or polypeptide to a subject having a mutated, absent, or non-functional version of the RNA, protein, or polypeptide or to a subject having a working version of the RNA, protein or polypeptide, wherein the RNA, protein, or polypeptide corresponds to a gene listed in Table 1.

TABLE 1

| Exemplary diseases and disorders and their associated genes that may be targeted for treatment | |
| --- | --- |
| Disease/Disorder(s) Type | Disease/Disorder and related Gene(s) |
| Age-related Macular Degeneration | Aber, Ccl2, Cc2, cp (ceruloplasmin), Timp3; Cathepsin D; VLDLR, Ccr2 |
| Blood and coagulation diseases and disorders | Anemia (CDAN1, CDA1, RPS19, DBA, PKLR, PK1, NT5C3, UMPH1, PSN1, RHAG, RH50A, NRAMP2, SPTB, ALAS2, ANH1, ASB, ABCB7, ABC7, ASAT); Bare lymphocyte syndrome (TAPBP, TPSN, TAP2, ABCB3, PSF2, RING11, MHC2TA, C2TA, RFX5, RFXAP, RFX5), Bleeding disorders (TBXA2R, P2RX1, P2X1); Factor H and factor H-like 1 (HF1, CFH, HUS); Factor V and factor VIII (MCFD2); Factor VII deficiency (F7); Factor X deficiency (F10); Factor XI deficiency (F11); Factor XII deficiency (F12, HAF); Factor XIIIA deficiency (F13A1, F13A); Factor XIIIB deficiency (F13B); Fanconi anemia (FANCA, FACA, FA1, FA, FAA, FAAP95, FAAP90, FLJ34064, FANCB, FANCC, FACC, BRCA2, FANCD1, FANCD2, FANCD, FACD, FAD, FANCE, FACE, FANCF, XRCC9, FANCG, BRIP1, BACH1, FANCJ, PHF9, FANCL, FANCM, KIAA1596); Hemophagocytic lymphohistiocytosis disorders (PRF1, HPLH2, UNC13D, MUNC13-4, HPLH3, HLH3, FHL3); Hemophilia A (F8, F8C, HEMA); Hemophilia B (F9, HEMB); Hemorrhagic disorders (PI, ATT, F5); Leukocyte deficiencies and disorders (ITGB2, CD18, LCAMB, LAD, EIF2B1, EIF2BA, EIF2B2, EIF2B3, EIF2B5, LVWM, CACH, CLE, EIF2B4); Sickle cell anemia (HBB); Thalassemia (HBA2, HBB, HBD, LCRB, HBA1) |
| Cell dysregulation and oncology diseases and disorders | B-cell non-Hodgkin lymphoma (BCL7A, BCL7); Leukemia (TAL1 TCL5, SCL, TAL2, FLT3, NBS1, NBS, ZNFN1A1, IK1, LYF1, HOXD4, HOX4B, BCR, CML, PHL, ALL, ARNT, KRAS2, RASK2, GMPS, AF10, ARHGEF12, LARG, KIAA0382, CALM, CLTH, CEBPA, CEBP, CHIC2, BTL, FLT3, KIT, PBT, LPP, NPM1, NUP214, D9S46E, CAN, CAIN, RUNX1, CBFA2, AML1, WHSC1L1, NSD3, FLT3, AF1Q, NPM1, NUMA1, ZNF145, PLZF, PML, MYL, STAT5B, AF10, CALM, CLTH, ARL11, ARLTS1, P2RX7, P2X7, BCR, CML, PHL, ALL, GRAF, NF1, VRNF, WSS, NFNS, PTPN11, PTP2C, SHP2, NS1, BCL2, CCND1, PRAD1, BCL1, TCRA, GATA1, GF1, ERYF1, NFE1, ABL1, NQO1, DIA4, NMOR1, NUP214, D9S46E, CAN, CAIN). |

TABLE 1-continued

Exemplary diseases and disorders and their associated
genes that may be targeted for treatment

| Disease/Disorder(s) Type | Disease/Disorder and related Gene(s) |
|---|---|
| Developmental | Angelman Syndrome (UBE3A, 15q11-13 deletion); Canavan disease (ASPA); Cri du chat (5P-, CTNND2); Down syndrome (Trisomy 21); Klinefelter syndrome (XXY, two or more X chromosomes in males); Prader-Willi syndrome (deletion of chromosome 15 segment); Turner syndrome (monosomy X, SHOX). |
| Drug addiction | Prkce (alcohol); Drd2; Drd4; ABAT (alcohol); GRIA2; Grm5; Grin1; Htr1b; Grin2a; Drd3; Pdyn; Gria1 (alcohol) |
| Inflammation and immune related diseases and disorders | AIDS (KIR3DL1, NKAT3, NKB1, AMB11, KIR3DS1, IFNG, CXCL12, SDF1); Autoimmune lymphoproliferative syndrome (TNFRSF6, APT1, FAS, CD95, ALPS1A); Combined immuno-deficiency, (IL2RG, SCIDX1, SCIDX, IMD4); HIV-1 (CCL5, SCYA5, D17S136E, TCP228), HIV susceptibility or infection (IL10, CSIF, CMKBR2, CCR2, CMKBR5, CCCKR5 (CCR5)); Immuno-deficiencies (CD3E, CD3G, AICDA, AID, HIGM2, TNFRSF5, CD40, UNG, DGU, HIGM4, TNFSF5, CD40LG, HIGM1, IGM, FOXP3, IPEX, AIID, XPID, PIDX, TNFRSF14B, TACI); Inflammation (IL-10, IL-1 (IL-1a, IL-1b), IL-13, IL-17 (IL-17a (CTLA8), IL-17b, IL-17c, IL-17d, IL-17f, II-23, Cx3cr1, ptpn22, TNFa, NOD2/CARD15 for IBD, IL-6, IL-12 (IL-12a, IL-12b), CTLA4, Cx3cl1); Severe combined immunodeficiencies (SCIDs) (JAK3, JAKL, DCLRE1C, ARTEMIS, SCIDA, RAG1, RAG2, ADA, PTPRC, CD45, LCA, IL7R, CD3D, T3D, IL2RG, SCIDX1, SCIDX, IMD4). |
| Metabolic, liver, kidney, and protein diseases and disorders | Amyloid neuropathy (TTR, PALB); Amyloidosis (APOA1, APP, AAA, CVAP, AD1, GSN, FGA, LYZ, TTR, PALB); Cirrhosis (KRT18, KRT8, CIRH1A, NAIC, TEX292, KIAA1988); Cystic fibrosis (CFTR, ABCC7, CF, MRP7); Glycogen storage diseases (SLC2A2, GLUT2, G6PC, G6PT, G6PT1, GAA, LAMP2, LAMPB, AGL, GDE, GBE1, GYS2, PYGL, PFKM); Hepatic adenoma, 142330 (TCF1, HNF1A, MODY3), Hepatic failure, early onset, and neurologic disorder (SCOD1, SCO1), Hepatic lipase deficiency (LIPC), Hepato-blastoma, cancer and carcinomas (CTNNB1, PDGFRL, PDGRL, PRLTS, AXIN1, AXIN, CTNNB1, TP53, P53, LFS1, IGF2R, MPRI, MET, CASP8, MCH5; Medullary cystic kidney disease (UMOD, HNFJ, FJHN, MCKD2, ADMCKD2); Phenylketonuria (PAH, PKU1, QDPR, DHPR, PTS); Polycystic kidney and hepatic disease (FCYT, PKHD1, ARPKD, PKD1, PKD2, PKD4, PKDTS, PRKCSH, G19P1, PCLD, SEC63). |
| Muscular/Skeletal diseases and disorders | Becker muscular dystrophy (DMD, BMD, MYF6), Duchenne Muscular Dystrophy (DMD, BMD); Emery-Dreifuss muscular dystrophy (LMNA, LMN1, EMD2, FPLD, CMD1A, HGPS, LGMD1B, LMNA, LMN1, EMD2, FPLD, CMD1A); Facio-scapulohumeral muscular dystrophy (FSHMD1A, FSHD1A); Muscular dystrophy (FKRP, MDC1C, LGMD2I, LAMA2, LAMM, LARGE, KIAA0609, MDC1D, FCMD, TTID, MYOT, CAPN3, CANP3, DYSF, LGMD2B, SGCG, LGMD2C, DMDA1, SCG3, SGCA, ADL, DAG2, LGMD2D, DMDA2, SGCB, LGMD2E, SGCD, SGD, LGMD2F, CMD1L, TCAP, LGMD2G, CMD1N, TRIM32, HT2A, LGMD2H, FKRP, MDC1C, LGMD2I, TTN, CMD1G, TMD, LGMD2J, POMT1, CAV3, LGMD1C, SEPN1, SELN, RSMD1, PLEC1, PLTN, EBS1); Osteopetrosis (LRP5, BMND1, LRP7, LR3, OPPG, VBCH2, CLCN7, CLC7, OPTA2, OSTM1, GL, TCIRG1, TIRC7, OC116, OPTB1); |

TABLE 1-continued

| Exemplary diseases and disorders and their associated genes that may be targeted for treatment | |
| --- | --- |
| Disease/Disorder(s) Type | Disease/Disorder and related Gene(s) |
| | Muscular atrophy (VAPB, VAPC, ALS8, SMN1, SMA1, SMA2, SMA3, SMA4, BSCL2, SPG17, GARS, SMAD1, CMT2D, HEXB, IGHMBP2, SMUBP2, CATF1, SMARD1); Tay-Sachs disease (HEXA). |
| Neurological and neuronal diseases and disorders | ALS (SOD1, ALS2, STEX, FUS, TARDBP, VEGF (VEGF-a, VEGF-b, VEGF-c); Alzheimer disease (APP, AAA, CVAP, AD1, APOE, AD2, PSEN2, AD4, STM2, APBB2, FE65L1, NOS3, PLAU, URK, ACE, DCP1, ACE1, MPO, PACIP1, PAXIP1L, PTIP, A2M, BLMH, BMH, PSEN1, AD3); Autism (Mecp2, BZRAP1, MDGA2, Sema5A, Neurexin 1, GLO1, MECP2, RTT, PPMX, MRX16, MRX79, NLGN3, NLGN4, KIAA1260, AUTSX2); Fragile X Syndrome (FMR2, FXR1, FXR2, mGLUR5); Huntington's disease and disease like disorders (HD, IT15, PRNP, PRIP, JPH3, JP3, HDL2, TBP, SCA17); Parkinson disease (NR4A2, NURR1, NOT, TINUR, SNCAIP, TBP, SCA17, SNCA, NACP, PARK1, PARK4, DJ1, PARK7, LRRK2, PARK8, PINK1, PARK6, UCHL1, PARK5, SNCA, NACP, PARK1, PARK4, PRKN, PARK2, PDJ, DBH, NDUFV2); Rett syndrome (MECP2, RTT, PPMX, MRX16, MRX79, CDKL5, STK9, MECP2, RTT, PPMX, MRX16, MRX79, x-Synuclein, DJ-1); Schizophrenia (Neuregulin1 (Nrg1), Erb4 (receptor for Neuregulin), Complexin1 (Cplx1), Tph1 Tryptophan hydroxylase, Tph2, Tryptophan hydroxylase 2, Neurexin 1, GSK3, GSK3a, GSK3b, 5-HTT (Slc6a4), COMT, DRD (Drd1a), SLC6A3, DAOA, DTNBP1, Dao (Dao1)); Secretase Related Disorders (APH-1 (alpha and beta), Presenilin (Psen1), nicastrin, (Ncstn), PEN-2, Nos1, Parp1, Nat1, Nat2); Trinucleotide Repeat Disorders (HTT (Huntington's Dx), SBMA/SMAX1/AR (Kennedy's Dx), FXN/X25 (Friedrich's Ataxia), ATX3 (Machado-Joseph's Dx), ATXN1 and ATXN2 (spinocerebellar ataxias), DMPK (myotonic dystrophy), Atrophin-1 and Atn1 (DRPLA Dx), CBP (Creb-BP - global instability), VLDLR (Alzheimer's), Atxn7, Atxn10). |
| Neoplasia | PTEN; ATM; ATR; EGFR; ERBB2; ERBB3; ERBB4; Notch1; Notch2; Notch3; Notch4; AKT; AKT2; AKT3; HIF; HIF1a; HIF3a; Met; HRG; Bcl2; PPAR alpha; PPAR gamma; WT1 (Wilms Tumor); FGF Receptor Family members (5 members: 1, 2, 3, 4, 5); CDKN2a; APC; RB (retinoblastoma); MEN1; VHL; BRCA1; BRCA2; AR (Androgen Receptor); TSG101; IGF; IGF Receptor; Igf1 (4 variants); Igf2 (3 variants); Igf 1 Receptor; Igf 2 Receptor; Bax; Bcl2; caspases family (9 members: 1, 2, 3, 4, 6, 7, 8, 9, 12); Kras; Apc |
| Ocular diseases and disorders | Age-related macular degeneration (Aber, Ccl2, Cc2, cp (ceruloplasmin), Timp3, cathepsin D, Vldlr, Ccr2); Cataract (CRYAA, CRYA1, CRYBB2, CRYB2, PITX3, BFSP2, CP49, CP47, CRYAA, CRYA1, PAX6, AN2, MGDA, CRYBA1, CRYB1, CRYGC, CRYG3, CCL, LIM2, MP19, CRYGD, CRYG4, BFSP2, CP49, CP47, HSF4, CTM, HSF4, CTM, MIP, AQP0, CRYAB, CRYA2, CTPP2, CRYBB1, CRYGD, CRYG4, CRYBB2, CRYB2, CRYGC, CRYG3, CCL, CRYAA, CRYA1, GJA8, CX50, CAE1, GJA3, CX46, CZP3, CAE3, CCM1, CAM, KRIT1); Corneal clouding and dystrophy (APOA1, TGFBI, CSD2, CDGG1, CSD, BIGH3, CDG2, TACSTD2, TROP2, M1S1, VSX1, RINX, PPCD, PPD, KTCN, COL8A2, FECD, PPCD2, PIP5K3, CFD); Cornea plana congenital (KERA, CNA2); Glaucoma (MYOC, TIGR, GLC1A, JOAG, GPOA, OPTN, GLC1E, FIP2, HYPL, NRP, CYP1B1, GLC3A, OPA1, NTG, NPG, CYP1B1, GLC3A); |

TABLE 1-continued

Exemplary diseases and disorders and their associated
genes that may be targeted for treatment

| Disease/Disorder(s) Type | Disease/Disorder and related Gene(s) |
|---|---|
| | Leber congenital amaurosis (CRB1, RP12, CRX, CORD2, CRD, RPGRIP1, LCA6, CORD9, RPE65, RP20, AIPL1, LCA4, GUCY2D, GUC2D, LCA1, CORD6, RDH12, LCA3); Macular dystrophy (ELOVL4, ADMD, STGD2, STGD3, RDS, RP7, PRPH2, PRPH, AVMD, AOFMD, VMD2). |
| Schizophrenia | Neuregulin1 (Nrg1); Erb4 (receptor for Neuregulin); Complexin1 (Cplx1); Tph1 Tryptophan hydroxylase; Tph2 Tryptophan hydroxylase 2; Neurexin 1; GSK3; GSK3a; GSK3b |
| Epilepsy myoclonic Lafora type 254780 | EPM2A, MELF, EPM2, NHLRC1, EPM2A, EPM2B |
| Duchenne muscular dystrophy type 310200 (3) | DMD, BMD |
| AIDS (delayed/rapid progression to (3)) | KIR3DL1, NKAT3, NKB1, AMB11, KIR3DS1 |
| AIDS (rapid progression to 609423 (3)) | IFNG |
| AIDS (resistance to (3)) | CXCL12, SDF1 |
| Alpha 1-Antitrypsin Deficiency | SERPINA1 [serpin peptidase inhibitor, clade A (alpha-1 antiproteinase, antitrypsin), member 1]; SERPINA2 [serpin peptidase inhibitor, clade A (alpha-1 antiproteinase, antitrypsin), member 2]; SERPINA3 [serpin peptidase inhibitor, clade A (alpha-1 antiproteinase, antitrypsin), member 3]; SERPINA5 [serpin peptidase inhibitor, clade A (alpha-1 antiproteinase, antitrypsin), member 5]; SERPINA6 [serpin peptidase inhibitor, clade A (alpha-1 antiproteinase, antitrypsin), member 6]; SERPINA7 [serpin peptidase inhibitor, clade A (alpha-1 antiproteinase, antitrypsin), member 7]; SERPLNA6 (serpin peptidase inhibitor, clade A (alpha-1 antiproteinase, antitrypsin), member 6) |

In some embodiments, the method of treating a subject in need thereof includes administering to the subject a delivery vehicle comprising a polynucleotide sequence encoding an RNA, polypeptide, or protein of interest operably linked to a synthetic promoter described herein, wherein expression of the RNA, polypeptide, or protein treats the disease or disorder.

In some embodiments, the synthetic promoters described herein are effective in treating a disease or disorder at a reduced dose (e.g., a dose comprising less of a delivery vehicle, e.g., comprising fewer viral particles comprising the promoter) compared to a CMV promoter or synthetic promoter of a greater length (e.g., promoters having at least 100 (e.g., at least 150, at least 175, at least 200, at least 225, at least 250, at least 275, at least 300, at least 350, at least 400, at least 450, at least 500, at least 550, at least 600, at least 650, at least 700, or more than 700) nucleic acids more than the synthetic promoter described herein)). In some embodiments, the synthetic promoters described herein are effective in treating a disease or disorder at a reduced dose compared to the CB7 promoter (SEQ ID NO: 9).

In some embodiments, the synthetic promoters described herein are effective in treating a disease or disorder at a reduced dose compared to a CMV promoter or synthetic promoter of a similar length, wherein the comparator promoter does not comprise a promoter-associated intronic sequence as described in Section IIA(i) herein (e.g., a synthetic promoter-associated intronic sequence, e.g., a promoter-associated intronic sequence having at least 95% sequence identity to SEQ ID NO: 1).

The reduced dose may be a decrease in a dose level (e.g., a decrease in the number of viral particles administered) of about 1.5-fold, 2-fold, 2.5-fold, 3-fold, 3.5-fold, 4-fold, 4.5-fold, 5-fold, 5.5-fold, 6-fold, 6.5-fold, 7-fold, 7.5-fold, 8-fold, 8.5-fold, 9-fold, 9.5-fold, 10-fold, 11-fold, 12-fold, 13-fold, 14-fold, 15-fold, 16-fold, 17-fold, 18-fold, 19-fold, or 20-fold, or more than 20-fold, e.g., about 1.5-fold to about 3-fold, about 3-fold to about 4.5-fold, about 4.5-fold to about 6-fold, about 6-fold to about 7.5-fold, about 7.5-fold to about 9-fold, about 9-fold to about 12-fold, about 12-fold to about 15-fold, or about 15-fold to about 20-fold relative to a comparator promoter.

Other embodiments of the present invention are described in the following Examples. The present invention is further illustrated by the following examples, which should not be construed as further limiting. The contents of Sequence Listing, figures and all references, patents and published patent applications cited throughout this application are expressly incorporated herein by reference.

III. Examples

The following are examples of the methods and compositions of the invention. It is understood that various other embodiments may be practiced, given the description provided herein.

Example 1. Design and Production of a Synthetic Promoter

Figures 1A, 1B:
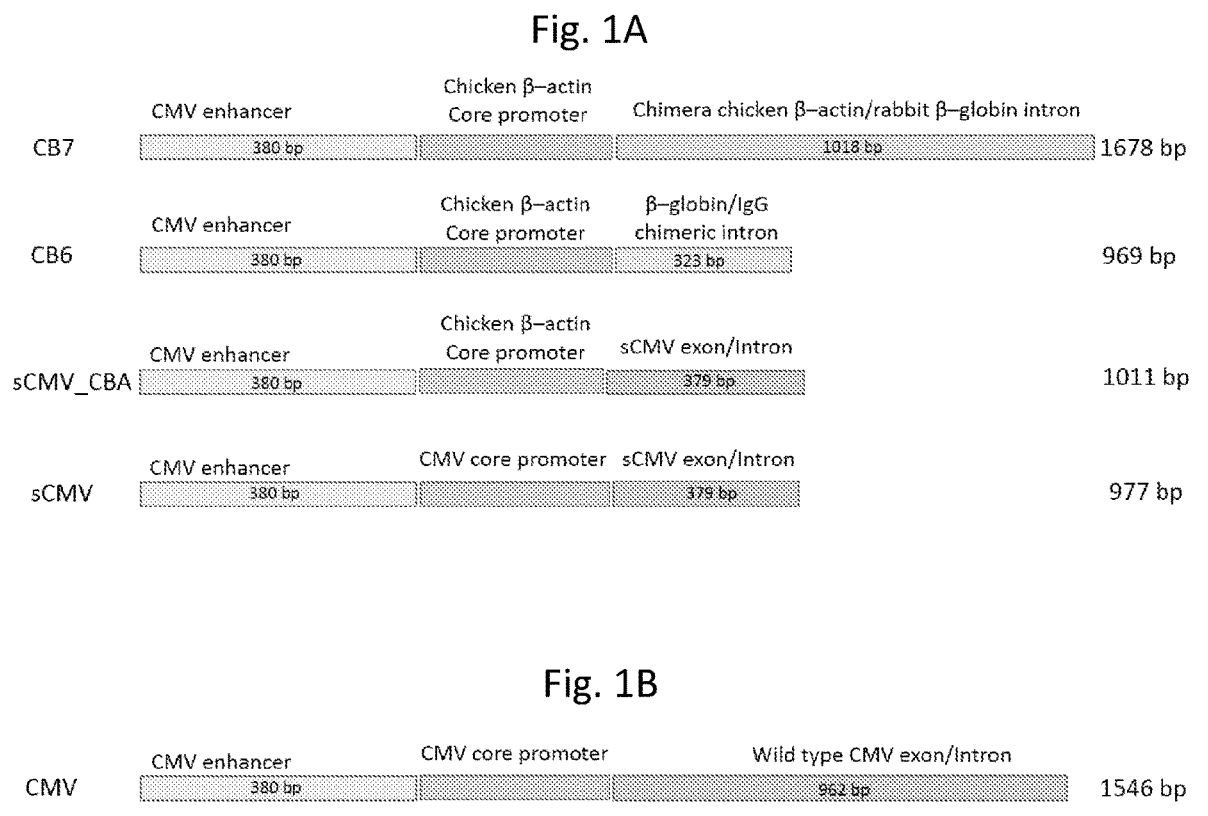

The length of regulatory elements (e.g., 5' regulatory constructs, e.g., promoters) is a limiting factor in the design of expression vectors. For example, the total operable capacity of a single chain rAAV vector is about 4.7 kb, and the total operable capacity of a self-complementary AAV (scAAV) is about 2.4 kb. These size limits must include both the transgene coding region and the 5' regulatory constructs (e.g., constructs including an enhancer, a core promoter and 5' intron as shown in FIGS. 1A and 1B).

The 5' regulatory construct CB7 (1678 bp; SEQ ID NO: 9; FIG. 1A and Table 2) is commonly used for single chain AAV vectors. For self-complementary AAV vectors, CB6 (969 bp; SEQ ID NO: 8; FIG. 1A and Table 2) is commonly used. Both CB7 and CB6 include the cytomegalovirus (CMV) enhancer (SEQ ID NO: 3) and the Chicken β-actin core promoter (SEQ ID NO: 4). CB7 further comprises a 1018 bp Chimera chicken β-actin/rabbit β-globin intron (SEQ ID NO: 11), and CB6 further comprises a β-globin/ IgG chimeric intron (SEQ ID NO: 10). The wild-type 5' UTR of CMV (SEQ ID NO: 13; FIG. 1B), which comprises the CMV enhancer (SEQ ID NO: 3), CMV core promoter (SEQ ID NO: 5), and wild-type CMV exon/intron sequence (SEQ ID NO: 2) is not used in gene therapy vectors by others because it can be silenced in vivo within a few weeks.

The goal of the present study was to design a novel construct that could constitutively provide better transgene expression in vivo than commonly used constructs, but with a comparable or shorter length, thus allowing more space for transgene coding regions in gene therapy vectors (e.g., rAAV vectors).

The novel construct sCMV-CBA (1011 bp: SEQ ID NO: 6; FIG. 1A and Table 2) includes the cytomegalovirus (CMV) enhancer (SEQ ID NO: 3), the Chicken β-actin core promoter (SEQ ID NO: 4), and a synthetic exon/intron (sCMV exon/intron; SEQ ID NO: 1). The synthetic exon/ intron is retained in the mature mRNA, but is not translated.

The sCMV exon/intron (SEQ ID NO: 1) sequence was based in part on the wild-type CMV exon/intron sequence (962 bp; SEQ ID NO: 12) that is present in the 5' UTR of the native CMV gene in many mammals (e.g., humans). The wild-type CMV exon/intron sequence is important for optimal protein expression, but has limited utility in expression vectors due to its large size. To generate a shorter exon/ intron sequence, the wild-type CMV exon/intron sequence was first truncated at different lengths: 250 bp, 450 bp and 650 bp. By comparing the transcript level, it was found that the length of the intron did not make a significant difference, so the shortest length (250 bp) was chosen as a template for further modification. To increase the promoter strength, a screen was performed in which a synthetic intron library (50 bp each) was inserted into to the middle of the 250 bp sequence. Based on the transcript level and expression level of a tested antibody, one of the introns was selected to construct the sCMV exon/intron (SEQ ID NO: 1) included in the sCMV-CBA (SEQ ID NO: 6).

TABLE 2

Design of promoter sequences

| Promoter construct | Enhancer | Core promoter | Intron |
|---|---|---|---|
| CB6 (SEQ ID NO: 8) | CMV enhancer (SEQ ID NO: 3) | Chicken β-actin core promoter (SEQ ID NO: 4) | β-globin/IgG chimeric (SEQ ID NO: 10) |
| CB7 (SEQ ID NO: 9) | CMV enhancer (SEQ ID NO: 3) | Chicken β-actin core promoter (SEQ ID NO: 4) | Chimera chicken β-actin/rabbit β-globin (SEQ ID NO: 11) |
| sCMV:CBA (SEQ ID NO: 6) | CMV enhancer (SEQ ID NO: 3) | Chicken β-actin core promoter (SEQ ID NO: 4) | sCMV exon/intron (SEQ ID NO: 1) |

TABLE 2-continued

Design of promoter sequences

| Promoter construct | Enhancer | Core promoter | Intron |
|---|---|---|---|
| sCMV:CMV (SEQ ID NO: 7) | CMV enhancer (SEQ ID NO: 3) | CMV core promoter (SEQ ID NO: 5) | sCMV exon/intron (SEQ ID NO: 1) |

Example 2. Synthetic Promoters Enhance Protein Expression in Transient Transfection A model IgG1 monoclonal antibody (mAb) was cloned into a mammalian expression vector containing one of the four promoter sequences provided in FIG. 1A and Table 2 such that the promoter sequence drove expression of the IgG1 mAb. The expression vectors were transfected into 293T cells by transient transfection. Cell supernatant was collected seven days post-transient transfection and tested for mAb expression by ELISA. The sCMV and sCMV-CBA promoters led to five-fold higher mAb expression than the CB6 promoter, which has a similar sequence length (FIG. 2). Surprisingly, expression level driven by the sCMV and sCMV-CBA promoters was comparable to the full-length CB7 promoter, which is about 700 base pairs longer (FIG. 2).

Example 3. A Synthetic Promoter Enhances AAV Gene Expression

Figure 3:
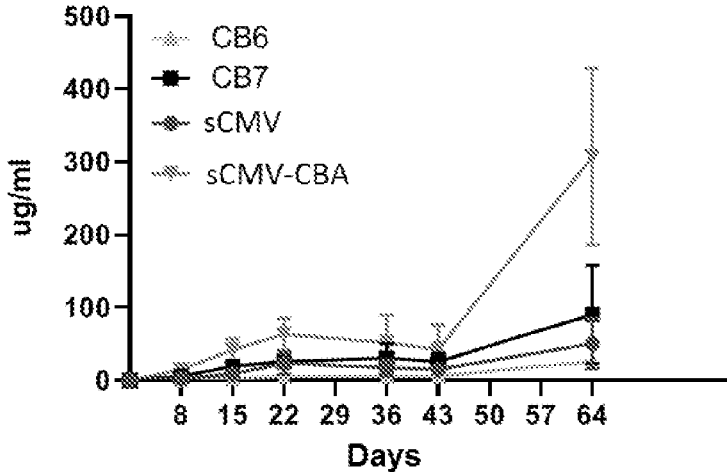
FIG. 3 is a scatter plot showing the in vivo expression level over time of an IgG1 mAb in C3H mice that were intramuscularly injected with $1 \times 10^{11}$ AAV particles comprising the IgG mAb sequence operably linked to the CB7, CB6, sCMV, or sCMV-CBA promoter sequence. Error bars represent the range in antibody concentration (µg/mL) values in serum observed in 4 replicates. These data were collected as described in Example 3.

Adeno-associated viruses (AAVs) that contained one of the four promoter sequences provided in FIG. 1A and Table 2 and a model human IgG1 mAb with expression driven by the promoter were constructed. C3H mice were divided into four groups (n=4 per group) and were intramuscularly injected with $1 \times 10^{11}$ adeno-associated virus (AAV) particles. Serum was collected prior to injection as well as weekly for 9 weeks and analyzed by ELISA to determine antibody concentration (FIG. 3). The sCMV-CBA promoter demonstrated significantly higher mAb expression in mice than the CB6, CB7, or sCMV promoters (FIG. 3).

Example 4. A Synthetic Promoter Enhances AAV Gene Expression Via IT Injection AAVs containing one of the four promoter sequences provided in FIG. 1A and Table 2 and a model human IgG1 mAb with expression driven by the promoter were constructed as described in Example 3.

Figure 4:
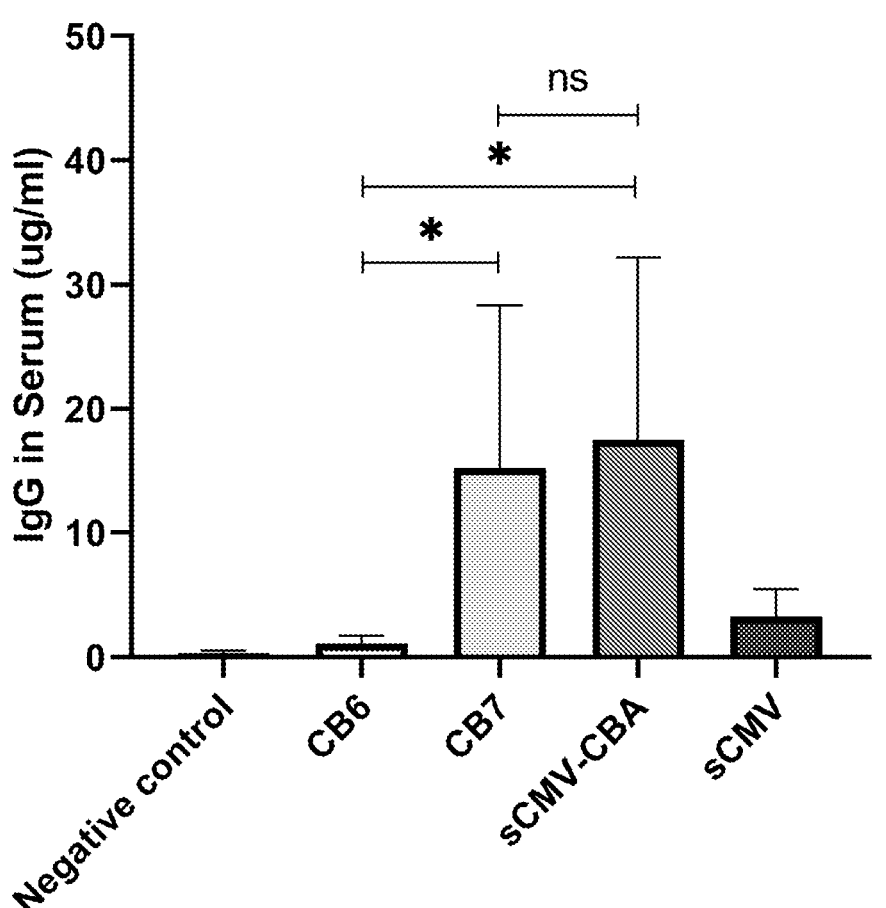
FIG. 4 is a bar graph showing the in vivo serum expression level of an IgG1 mAb in FVB/NJ mice that were intrathecally (I.T.) injected with $2.5 \times 10^{10}$ AAV particles comprising the IgG mAb sequence operably linked to the CB7, CB6, sCMV, or sCMV-CBA promoter sequence. Error bars represent the range in antibody concentration (µg/mL) values in serum observed in 4-5 replicates at 3 weeks after injection, as measured using ELISA. Asterisk indicates a significant difference between groups. For CB6 vs. CB7, p=0.0430. For CB6 vs. sCMV-CBA, p=0.0390. For CB7 vs. sCMV-CBA, p=0.8123 (NS: not significant). These data were collected as described in Example 4.

FVB/NJ mice were divided into four groups (n=4-5 males per group) and were intrathecally injected with $2.5 \times 10^{10}$ AAV particles. Serum was collected three weeks after injection and analyzed by ELISA to determine the antibody concentration. The sCMV-CBA promoter led to a significant increase in mAb expression relative to the CB6 promoter, and a comparable expression level compared with the CB7 promoter (FIG. 4).

Figure 5:
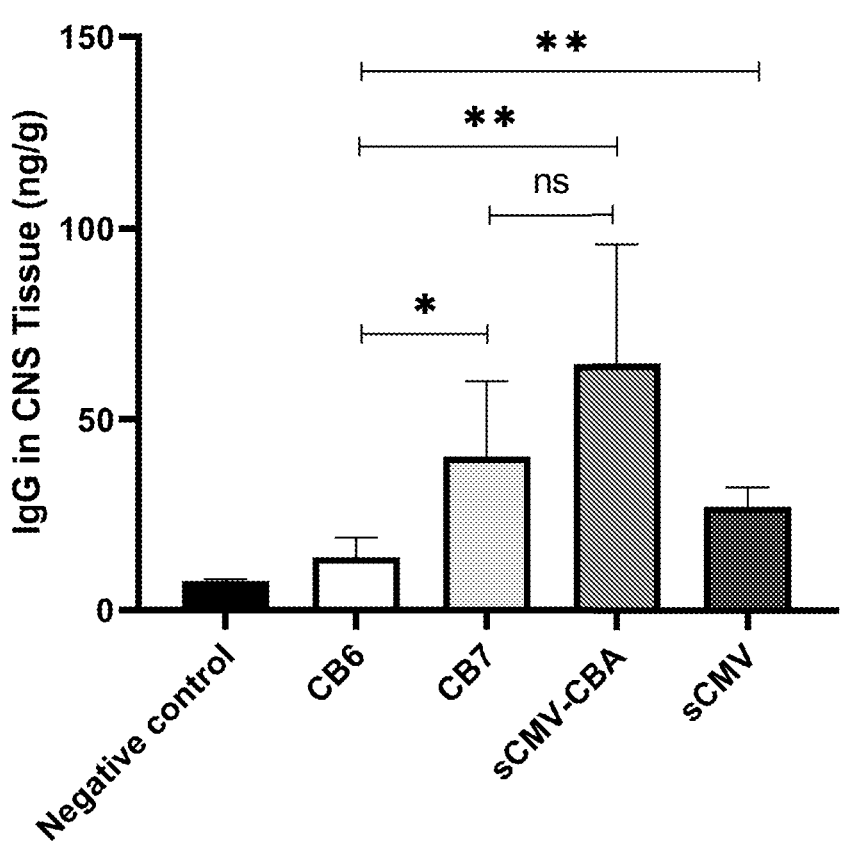
FIG. 5 is a bar graph showing the in vivo expression level in central nervous system (CNS) tissue of an IgG1 mAb in FVB/NJ mice that were intrathecally (I.T.) injected with $2.5 \times 10^{10}$ AAV particles comprising the IgG mAb sequence operably linked to the CB7, CB6, sCMV, or sCMV-CBA promoter sequence. Error bars represent the range in antibody concentration (µg/mL) values in CNS tissue observed in 4-5 replicates at 3 weeks after injection, as measured using ELISA. Asterisk indicates a significant difference between groups. For CB6 vs. CB7, p=0.0194. For CB6 vs. sCMV-CBA, p=0.0083. For CB6 vs. sCMV, p=0.0060. For CB7 vs. sCMV-CBA, p=0.1967 (NS: not significant). These data were collected as described in Example 4.

For FVB/NJ mice treated as described above, spinal cord tissue was collected three weeks after injection and the tissue lysate was analyzed by ELISA to determine the antibody concentration. The sCMV-CBA promoter led to a significant increase in mAb expression in the spinal cord relative to the CB6 promoter, and a comparable mAb expression level compared with the CB7 promoter (FIG. 5).

Example 5. Synthetic Promoters for Gene Therapy

In some embodiments, a synthetic promoter described herein is incorporated into a delivery vehicle (e.g., a vector (e.g., a viral vector (e.g., an AAV or lentiviral vector))) and is operably linked to a nucleic acid encoding a therapeutic protein or polypeptide for use in treating a subject having a disease or disorder (e.g., a genetic mutation). For example, a subject having a genetic mutation in a single gene (e.g., any gene of Table 1) can be treated by the delivery of a delivery vehicle capable of expressing a therapeutic protein or polypeptide by a synthetic promoter described herein and subsequent expression of a wild-type (WT) (e.g., non-mutant) gene. In other examples, the delivery vehicle is used to deliver a beneficial peptide or polypeptide whose gene is not necessarily mutated in the subject. For delivery to a cell, a delivery vehicle (e.g., a viral vector) can be designed with polynucleotides encoding the synthetic promoter operably linked to a polynucleotide encoding the target gene of interest. The smaller size of the synthetic promoter allows for treatment of diseases requiring therapeutic peptides or proteins encoded by larger coding sequences, increasing the number of treatable diseases by viral vector gene therapy. In yet another example, a heterologous gene for the gene therapy might be used to elicit an immune response in the subject that would be beneficial for the treatment of a particular disease.

Example 6. A Synthetic Promoter Enhances AAV Expression of a Nanobody

BALB/cJ mice were divided into 3 groups (n=5 males per group) and were intramuscularly injected with $1\times10^{11}$ AAV particles. Each group received particles containing a testing nanobody with expression driven by one of the CB6, sCMV-CBA, and sCMV promoter sequences. The CB7 promoter was not included in this study due to the limited capacity of the self-complementary AAV.

Figure 6:
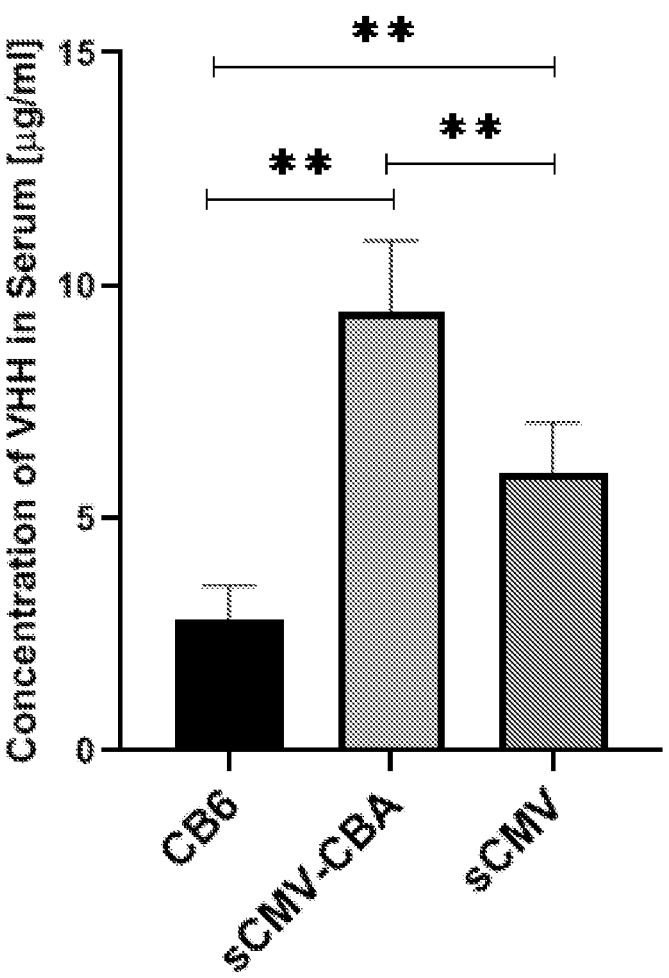
FIG. 6 is a bar graph showing the in vivo serum expression level of a VHH (nanobody) in BALB/cJ mice that were intramuscularly (I.M.) injected with $1 \times 10^{11}$ Self-complementary AAV (scAAV) particles comprising the VHH (Nanobody) sequence operably linked to the CB6, sCMV, or sCMV-CBA promoter sequence. Error bars represent the range in antibody concentration (µg/mL) values in serum observed in 5 replicates at 4 weeks after injection, as measured using ELISA. Asterisk indicates a significant difference between groups. For CB6 vs. sCMV-CBA, p<0.001. For CB6 vs. sCMV, p=0.0006. For sCMV-CBA vs. sCMV, p=0.0036. These data were collected as described in Example 6.

Serum was collected 4 weeks after injection and analyzed by ELISA to determine the nanobody concentration. The sCMV-CBA promoter led to a significant increase in nanobody expression in mice relative to the CB6 promoter; thus, the sCMV-CBA promoter enhanced self-complementary AAV gene expression by intramuscular injection (FIG. 6).

Other Embodiments

Although the foregoing invention has been described in some detail by way of illustration and example for purposes of clarity of understanding, the descriptions and examples should not be construed as limiting the scope of the invention. The disclosures of all patent and scientific literature cited herein are expressly incorporated in their entirety by reference.

What is claimed is:

1. A promoter-associated intronic sequence comprising a nucleic acid sequence having at least 95% sequence identity to SEQ ID NO: 1.

2. A promoter-associated intronic sequence comprising the nucleic acid sequence of SEQ ID NO: 1.

3. A polynucleotide comprising the promoter-associated intronic sequence of claim 1 and a nucleic acid sequence encoding an enhancer sequence.

4. A promoter sequence comprising a nucleic acid sequence comprising an enhancer sequence, a nucleic acid sequence comprising a core promoter sequence, and the promoter-associated intronic sequence of claim 1.

5. The promoter sequence of claim 4, wherein the nucleic acid sequence comprising the core promoter sequence is:
   (a) operably linked at its 5' end to the 3' end of the enhancer sequence; and
   (b) operably linked at its 3' end to the 5' end of the promoter-associated intronic sequence.

6. The promoter sequence of claim 4, wherein:
   (i) the enhancer sequence is a CMV enhancer sequence; and/or
   (ii) the core promoter sequence is a chicken β-actin core promoter sequence.

7. The promoter sequence of claim 6, wherein:
   (i) the CMV enhancer sequence comprises a nucleic acid sequence having at least 95% identity to SEQ ID NO: 3; and/or
   (ii) the chicken β-actin core promoter sequence comprises a nucleic acid sequence having at least 95% identity to SEQ ID NO: 4.

8. The promoter sequence of claim 4, wherein the promoter sequence is operably linked to a target nucleic acid sequence.

9. The promoter sequence of claim 8, wherein the target nucleic acid sequence encodes an RNA.

10. The promoter sequence of claim 9, wherein:
   (a) the RNA is a miRNA, an siRNA, a shRNA, or a guide RNA (gRNA); and/or
   (b) the target nucleic acid sequence encodes an mRNA that is translated to a protein or polypeptide.

11. A promoter sequence comprising a nucleic acid sequence having at least 95% identity to SEQ ID NO: 6.

12. A delivery vehicle comprising the polynucleotide of claim 3.

13. The delivery vehicle of claim 12, wherein the delivery vehicle is a viral vector, an adeno-associated viral (AAV) vector, or a lentiviral vector.

14. A host cell comprising the polynucleotide of claim 3.

15. A method of producing an RNA, protein, or polypeptide in a cell, the method comprising:
   (a) providing a polynucleotide comprising a promoter sequence of claim 4 and a target nucleic acid sequence encoding the RNA, protein, or polypeptide, wherein the promoter sequence is operably linked to the target nucleic acid sequence;
   (b) introducing the polynucleotide into a host cell;
   (c) exposing the host cell comprising the polynucleotide to conditions suitable for expression of the RNA, protein, or polypeptide, thereby producing the RNA, protein, or polypeptide; and
   (d) recovering the RNA, protein, or polypeptide from the host cell or host cell culture medium.

16. A method of expressing an RNA, protein, or polypeptide in a subject, the method comprising administering to the subject an effective amount of a delivery vehicle comprising a polynucleotide comprising a promoter sequence of claim 4 and a target nucleic acid sequence encoding the RNA, protein, or polypeptide, wherein the promoter sequence is operably linked to the target nucleic acid sequence.

17. The method of claim 16, wherein the delivery vehicle is a vector.

18. The method of claim 17, wherein the vector is a viral vector, an AAV vector, a single chain rAAV vector, a self-complementary AAV, or a lentiviral vector.

19. A method of inducing an immune response in a subject, the method comprising administering to the subject an effective amount of a delivery vehicle comprising a polynucleotide comprising a promoter sequence of claim 4 and a target nucleic acid sequence encoding an RNA, protein, or polypeptide, wherein the promoter sequence is operably linked to the target nucleic acid sequence, and wherein expression of the RNA, protein, or polypeptide elicits an immune response.

* * * * *